US012773269B2

(12) United States Patent
Soper

(10) Patent No.: US 12,773,269 B2
(45) Date of Patent: Oct. 27, 2026

(54) SYSTEMS FOR ENHANCED REGISTRATION OF PATIENT ANATOMY

(71) Applicant: Intuitive Surgical Operations, Inc., Sunnyvale, CA (US)

(72) Inventor: Timothy D. Soper, San Jose, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 1090 days.

(21) Appl. No.: 17/439,015

(22) PCT Filed: Mar. 11, 2020

(86) PCT No.: PCT/US2020/021989
§ 371 (c)(1),
(2) Date: Sep. 14, 2021

(87) PCT Pub. No.: WO2020/190584
PCT Pub. Date: Sep. 24, 2020

(65) Prior Publication Data

US 2022/0142714 A1 May 12, 2022

Related U.S. Application Data

(60) Provisional application No. 62/818,982, filed on Mar. 15, 2019.

(51) Int. Cl.
*A61B 34/20* (2016.01)
*A61B 34/00* (2016.01)
(Continued)

(52) U.S. Cl.
CPC .............. *A61B 34/20* (2016.02); *A61B 34/10* (2016.02); *A61B 34/25* (2016.02); *A61B 34/37* (2016.02);
(Continued)

(58) Field of Classification Search
None
See application file for complete search history.

(56) References Cited

U.S. PATENT DOCUMENTS

2007/0225553 A1* 9/2007 Shahidi .................. A61B 90/36 600/103
2009/0227861 A1* 9/2009 Ganatra ................. A61B 34/20 600/424
(Continued)

FOREIGN PATENT DOCUMENTS

WO WO-2017030915 A1 * 2/2017 ........... A61B 1/0016
WO WO-2018006046 A1 * 1/2018 ............. A61B 34/32
(Continued)

OTHER PUBLICATIONS

International Preliminary Report on Patentability for Application No. PCT/US2020/021989 mailed on Sep. 30, 2021, 12 pages.
(Continued)

*Primary Examiner* — Ryan F Pitaro
*Assistant Examiner* — Bernard E Cothran
(74) *Attorney, Agent, or Firm* — Haynes & Boone, LLP.

(57) ABSTRACT

A system comprises a medical instrument, a tracking system configured to monitor a position of the medical instrument, and a processor communicatively coupled to the medical instrument and the tracking system. The processor is configured to generate a plurality of model points of an anatomic structure of a patient, receive a set of measured points of a first portion of the anatomic structure of the patient from the tracking system while the medical instrument is disposed within the anatomic structure of the patient, the set of measured points being associated with a first motion cycle of the medical instrument, map the set of measured points to a first model path of the plurality of model paths, and register the set of measured points with a first portion of the plurality
(Continued)

of model points, the first portion associated with the first model path of the plurality of model paths.

17 Claims, 17 Drawing Sheets

(51) Int. Cl.
*A61B 34/10* (2016.01)
*A61B 34/30* (2016.01)
*A61B 34/37* (2016.01)
*A61B 90/00* (2016.01)

(52) U.S. Cl.
CPC .............. *A61B 34/71* (2016.02); *A61B 90/37* (2016.02); *A61B 2034/105* (2016.02); *A61B 2034/2051* (2016.02); *A61B 2034/2055* (2016.02); *A61B 2034/2059* (2016.02); *A61B 2034/2061* (2016.02); *A61B 2034/2068* (2016.02); *A61B 2034/2074* (2016.02); *A61B 2034/301* (2016.02); *A61B 2090/3735* (2016.02); *A61B 2090/374* (2016.02); *A61B 2090/3762* (2016.02); *A61B 2090/378* (2016.02)

(56) References Cited

U.S. PATENT DOCUMENTS

| | | | |
|---|---|---|---|
| 2013/0303892 | A1 | 11/2013 | Zhao et al. |
| 2018/0235709 | A1 | 8/2018 | Donhowe et al. |

FOREIGN PATENT DOCUMENTS

| | | | |
|---|---|---|---|
| WO | WO-2018085287 | A1 | 5/2018 |
| WO | WO-2018144636 | A1 | 8/2018 |
| WO | WO-2018144726 | A1 | 8/2018 |

OTHER PUBLICATIONS

International Search Report and Written Opinion for Application No. PCT/US2020/021989, mailed Jun. 8, 2020, 20 pages.

Vertut, Jean and Phillipe Coiffet, Robot Technology: “Teleoperation and Robotics Evolution and Development,” English translation, Prentice-Hall, Inc., Inglewood Cliffs, NJ, USA 1986, vol. 3A, 332 pages.

* cited by examiner

SYSTEMS FOR ENHANCED REGISTRATION OF PATIENT ANATOMY

CROSS-REFERENCE TO RELATED APPLICATIONS

This application is the U.S. national stage of International Application No. PCT/US2020/021989, filed Mar. 11, 2020, which designated the U.S. and claims priority to and the benefit of U.S. Provisional Application 62/818,982 filed Mar. 15, 2019, both of which are incorporated by reference herein in their entirety.

FIELD

The present disclosure is directed to systems and methods for conducting an image-guided procedure, and more particularly to systems and methods for using registered real-time images and prior-time anatomic images during an image-guided procedure.

BACKGROUND

Minimally invasive medical techniques are intended to reduce the amount of tissue that is damaged during medical procedures, thereby reducing patient recovery time, discomfort, and harmful side effects. Such minimally invasive techniques may be performed through natural orifices in a patient anatomy or through one or more surgical incisions. Through these natural orifices or incisions an operator may insert minimally invasive medical instruments (including surgical, diagnostic, therapeutic, or biopsy instruments) to reach a target tissue location. To assist with reaching the target tissue location, the location and movement of the medical instruments may be correlated with pre-operative or intra-operative images of the patient anatomy. With the image-guided instruments correlated to the images, the instruments may navigate natural or surgically created passageways in anatomic systems such as the lungs, the colon, the intestines, the kidneys, the heart, the circulatory system, or the like. However, usually an operator does not have sufficient knowledge about the quality (e.g., accuracy, completeness, validity, consistency) of such correlation, which may cause uncertainty in the image-guided procedure.

Accordingly, it would be advantageous to provide improved registration for performing image-guided procedures.

SUMMARY

Embodiments of the invention are best summarized by the claims that follow the description.

Consistent with some embodiments, a system comprises a medical instrument, a tracking system configured to monitor a position of the medical instrument, and a processor communicatively coupled to the medical instrument and the tracking system. The processor is configured to generate a plurality of model points of a model of an anatomic structure of a patient, the plurality of model points being associated with coordinates of a model space, wherein the model of the anatomic structure of the patient includes a plurality of model paths, each model path of the plurality of model paths associated with a portion of the plurality of the model points. The processor is also configured to receive a set of measured points of a first portion of the anatomic structure of the patient from the tracking system, while the medical instrument is disposed within the anatomic structure of the patient, wherein the set of measured points is associated with a first motion cycle of a plurality of motion cycles of the medical instrument. The processor is further configured to map the set of measured points to a first model path of the plurality of model paths. The processor is configured to register the set of measured points with a first portion of the plurality of model points, the first portion of the plurality of model points associated with the first model path of the plurality of model paths.

Consistent with some embodiments, a method comprises generating a plurality of model points of a model of an anatomic structure of a patient, the plurality of model points being associated with a model space, wherein the model of the anatomic structure of the patient includes a plurality of model paths, each model path of the plurality of model paths associated with a portion of the plurality of model points. The method also comprises collecting a set of measured points of a first portion of the anatomic structure of the patient from a medical instrument while the medical instrument is disposed within the anatomic structure of the patient, wherein the set of measured points is associated with a first motion cycle of the medical instrument. The method further includes mapping the set of measured points to a first model path of the plurality of model paths. Finally, the method includes registering the set of measured points with a first portion of the plurality of model points, the first portion of the plurality of model points associated with the first model path of the plurality of model paths.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTIONS OF THE DRAWINGS

Figure 2B:
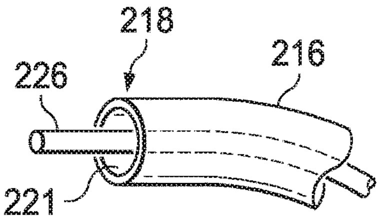
FIG. 2B is a simplified diagram of a medical instrument with an extended medical tool according to some embodiments.
Figure 2A:
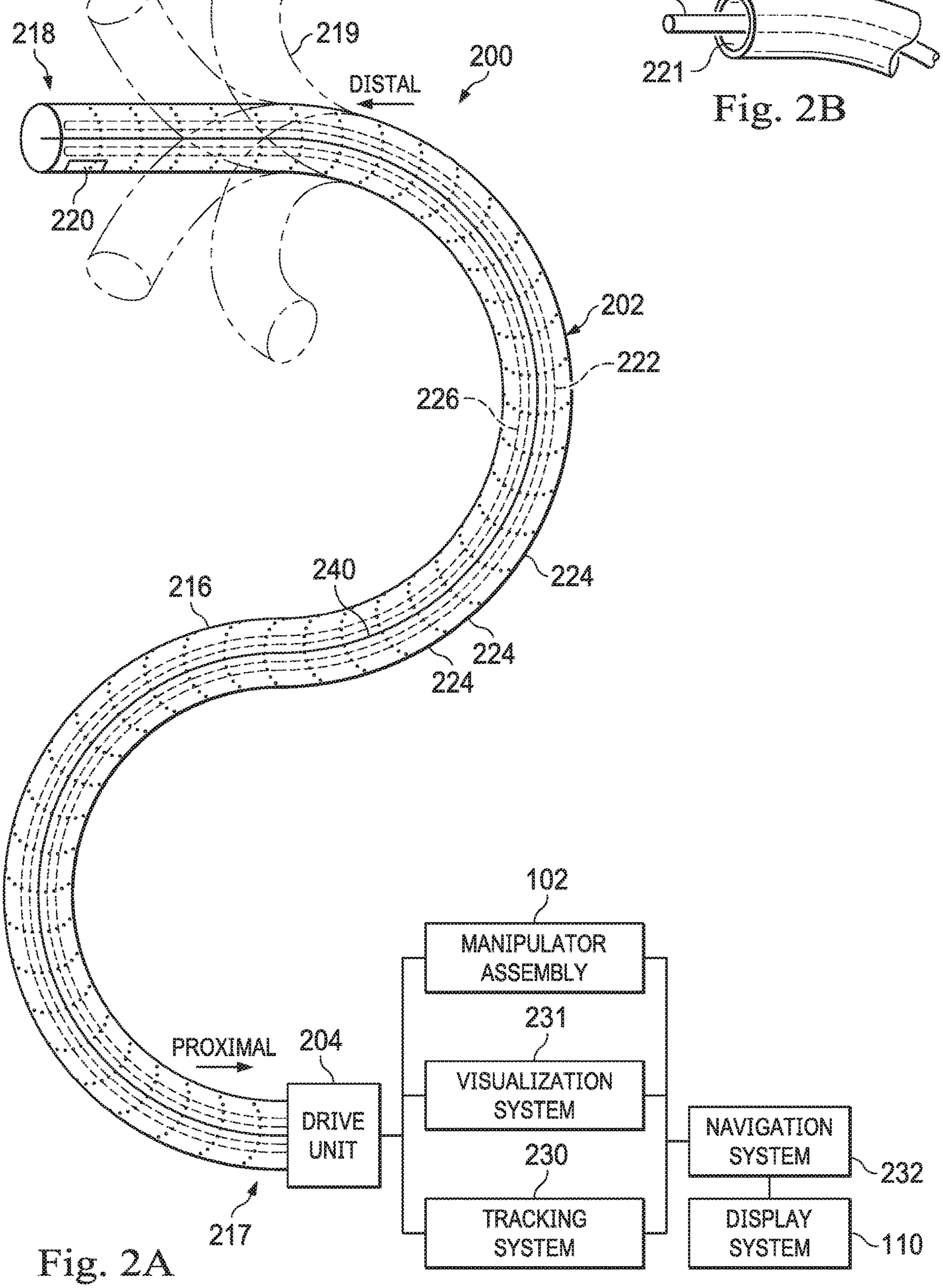
FIG. 2A is a simplified diagram of a medical instrument system according to some embodiments.
Figure 3A:
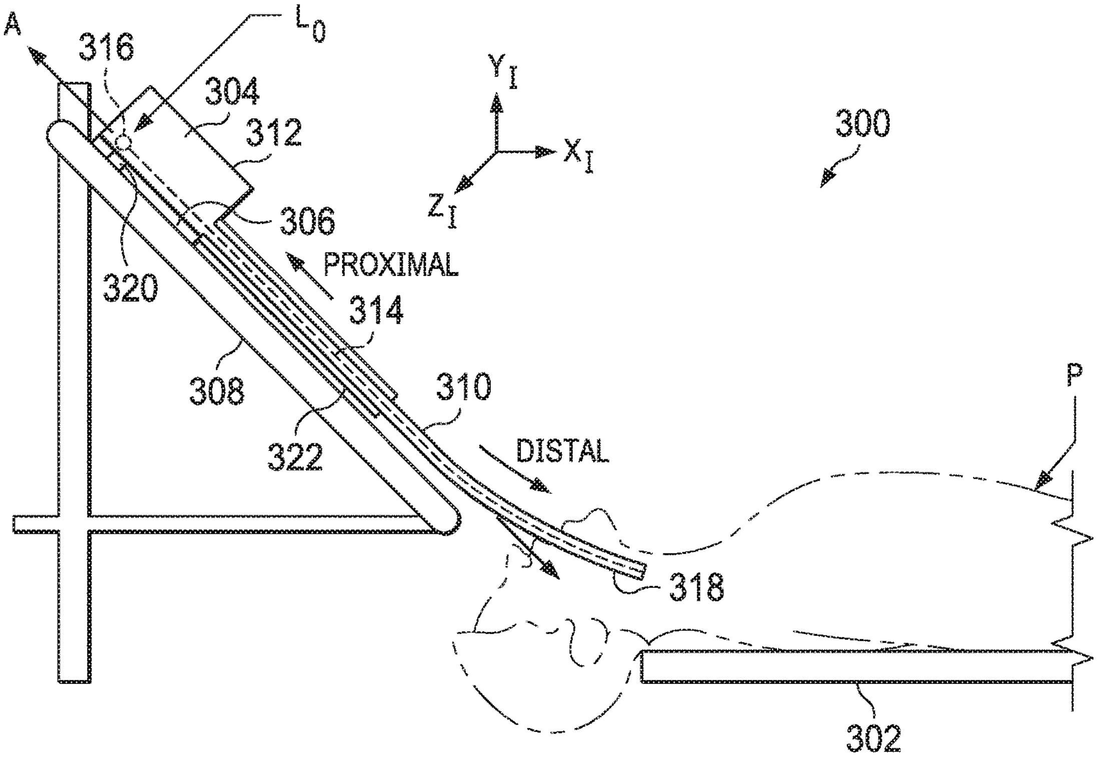
FIGS. 3A and 3B are simplified diagrams of side views of a patient coordinate space including a medical instrument mounted on an insertion assembly according to some embodiments.
Figure 3B:
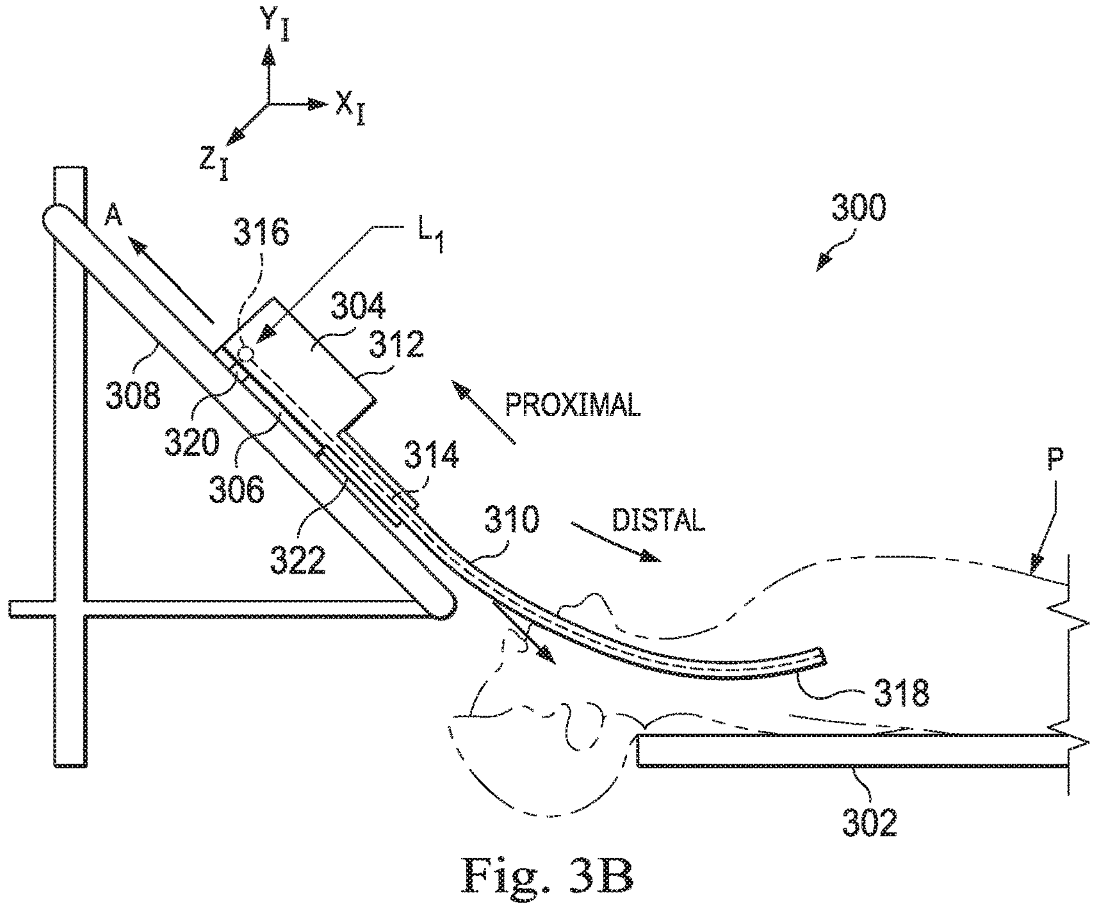
Figure 4A:
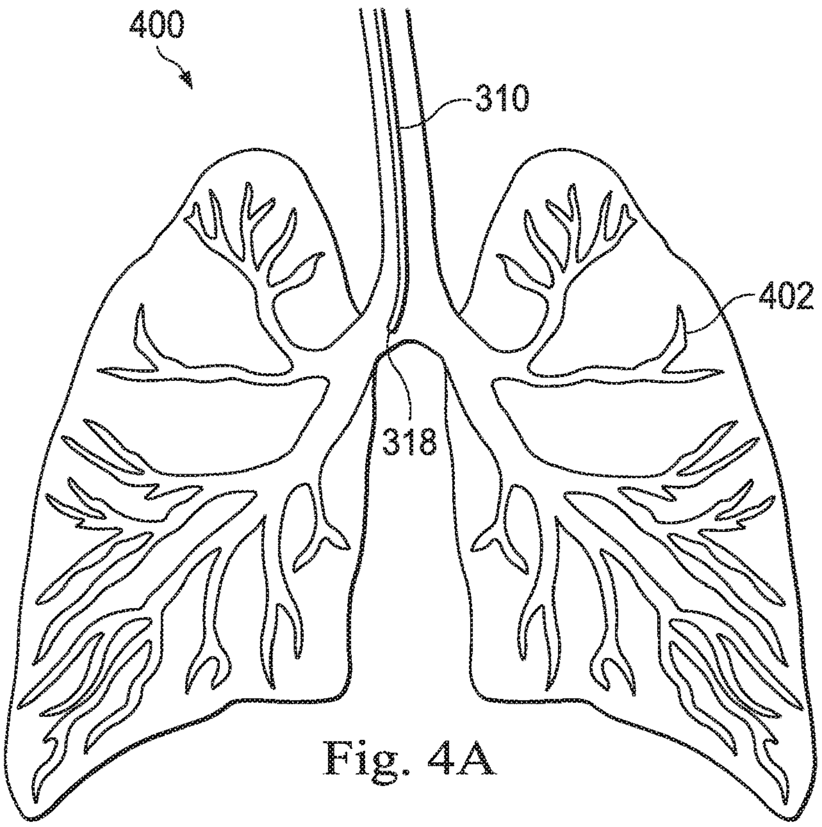
Figure 4B:
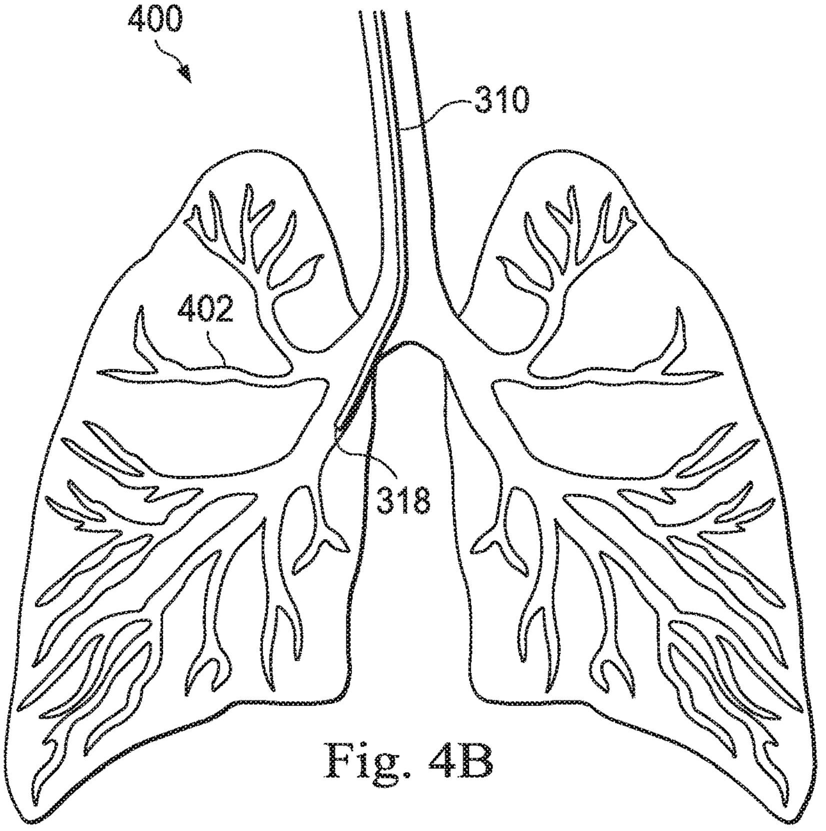
Figure 4C:
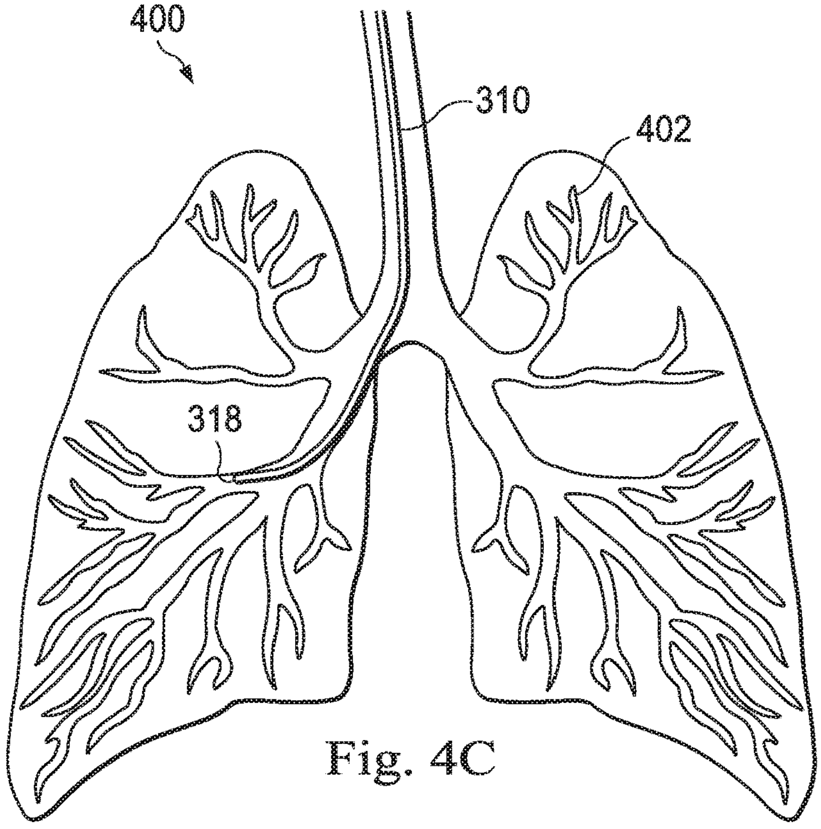
Figure 4D:
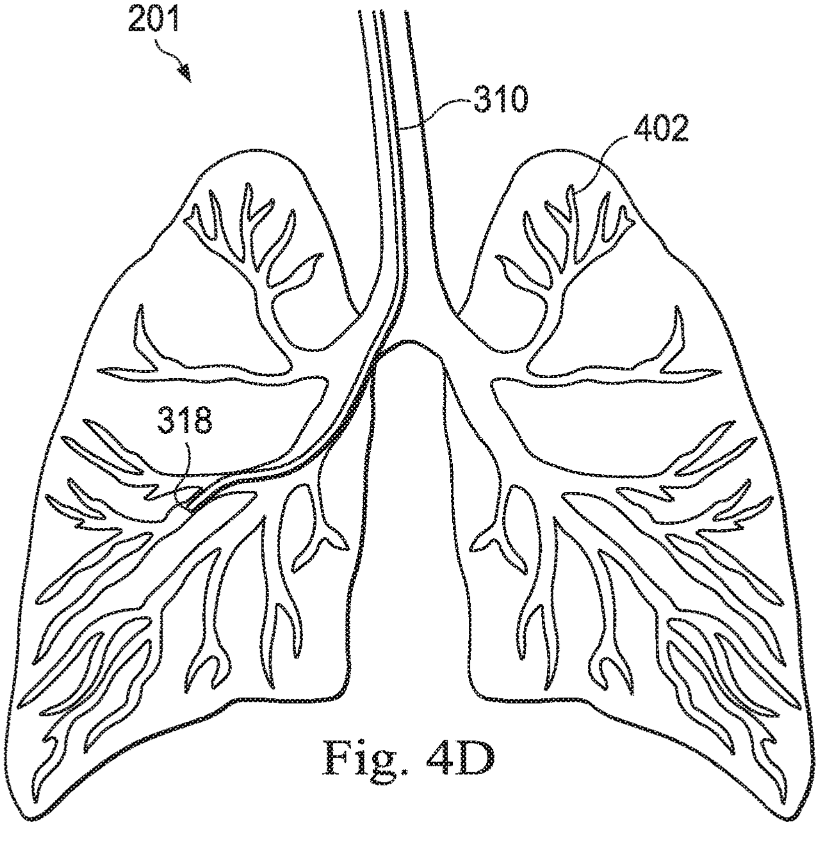

FIGS. 4A, 4B, 4C, and 4D illustrate the distal end of the medical instrument system of FIGS. 2, 3A, 3B, during insertion within a human lung according to some embodiments.

Figure 5:
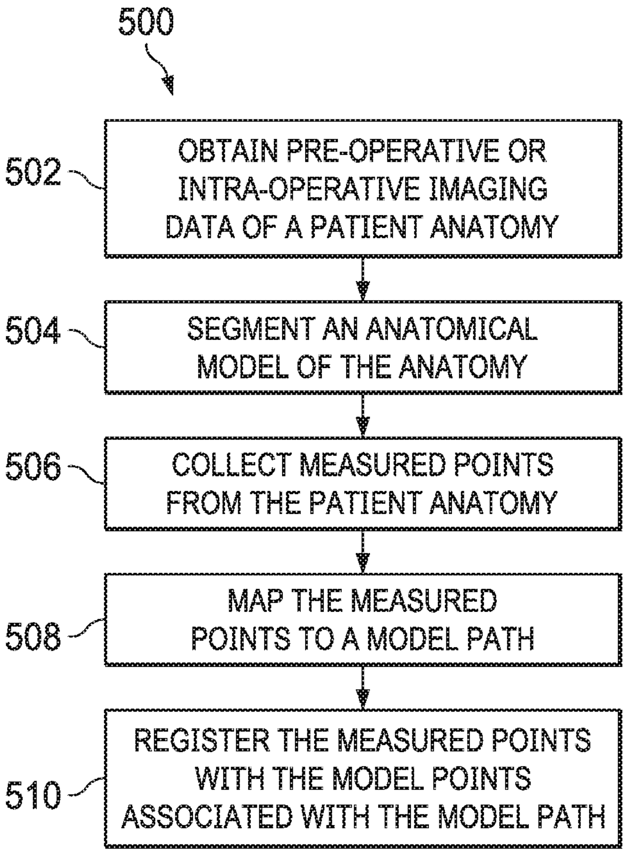

FIG. 5 is a flow chart illustrating a method of an image-guided surgical procedure or a portion thereof according to some embodiments.

FIGS. 6A-6G illustrate steps in segmentation processes that generate a model of an anatomy of a patient P for registration according to some embodiments.

Figure 6A:
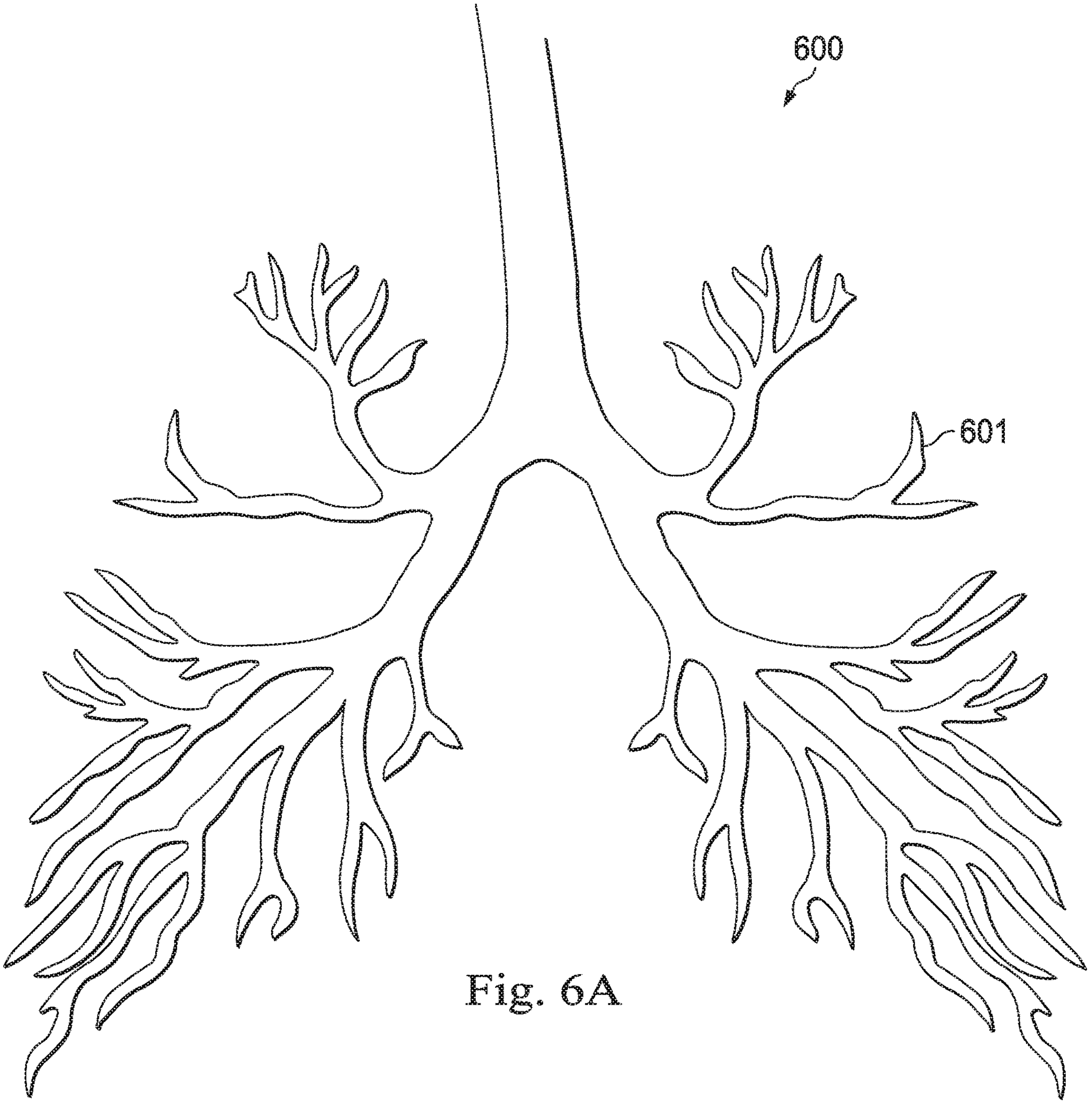
Figure 6B:
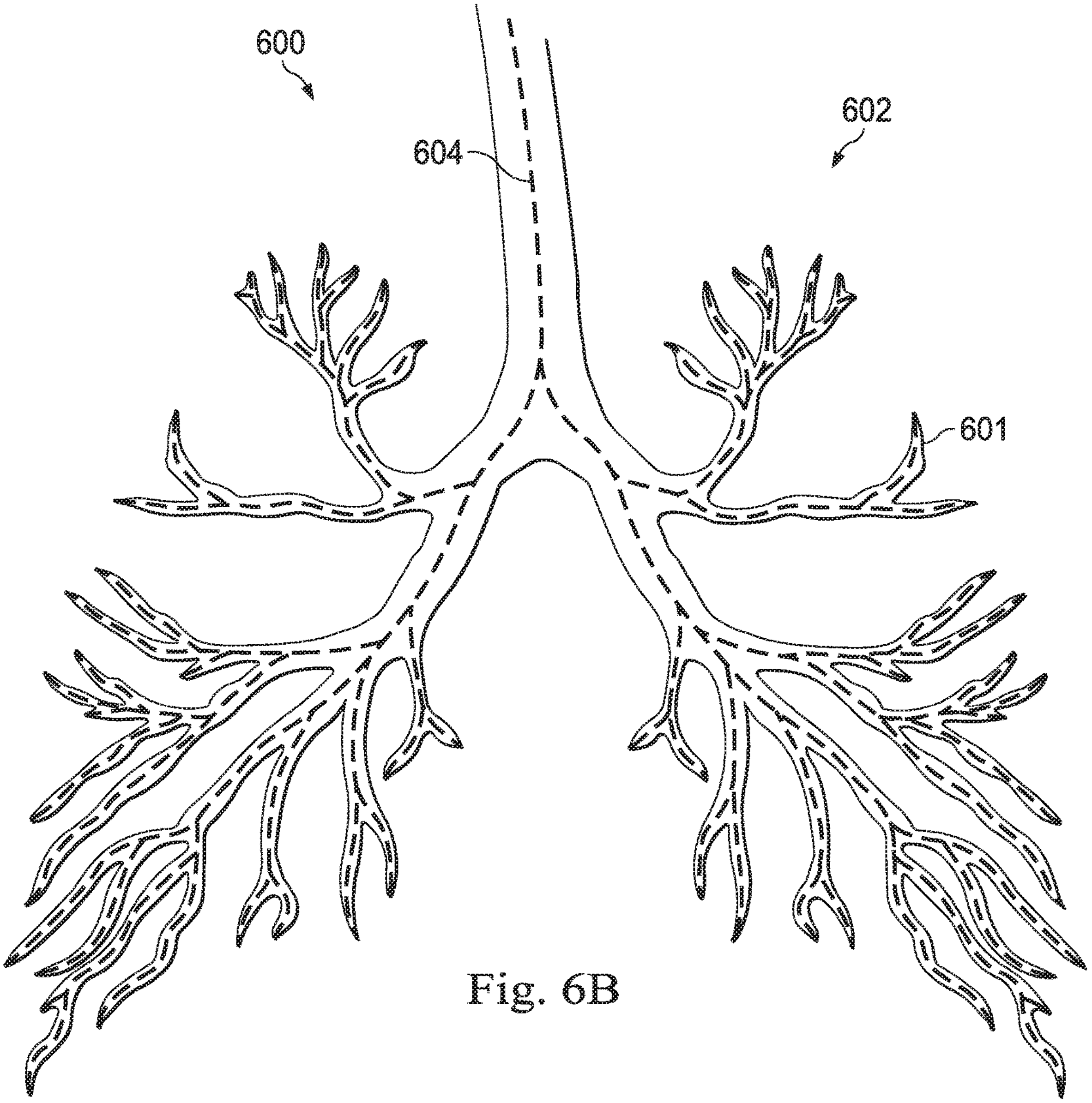
Figure 6C:
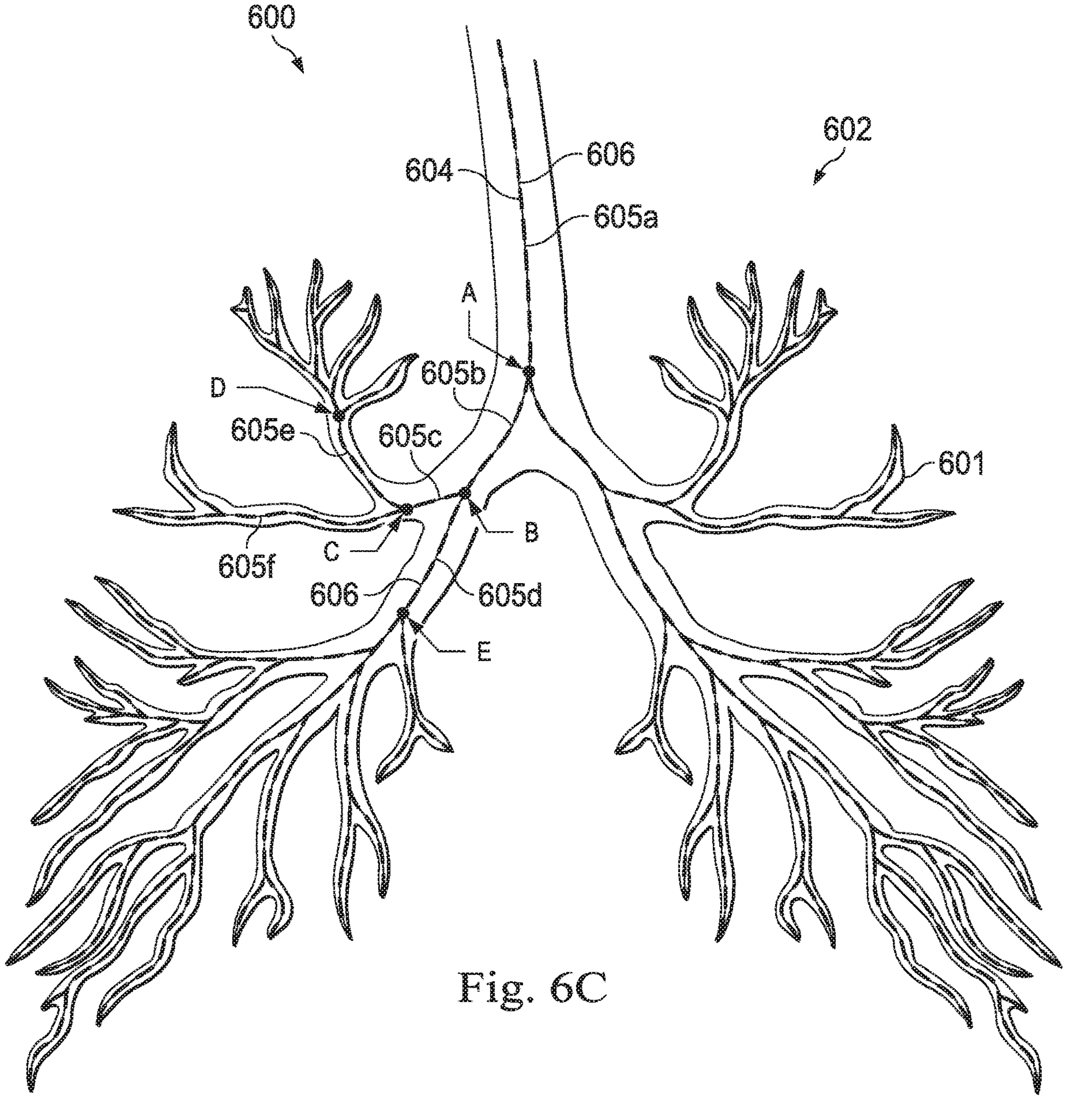
Figure 6D:
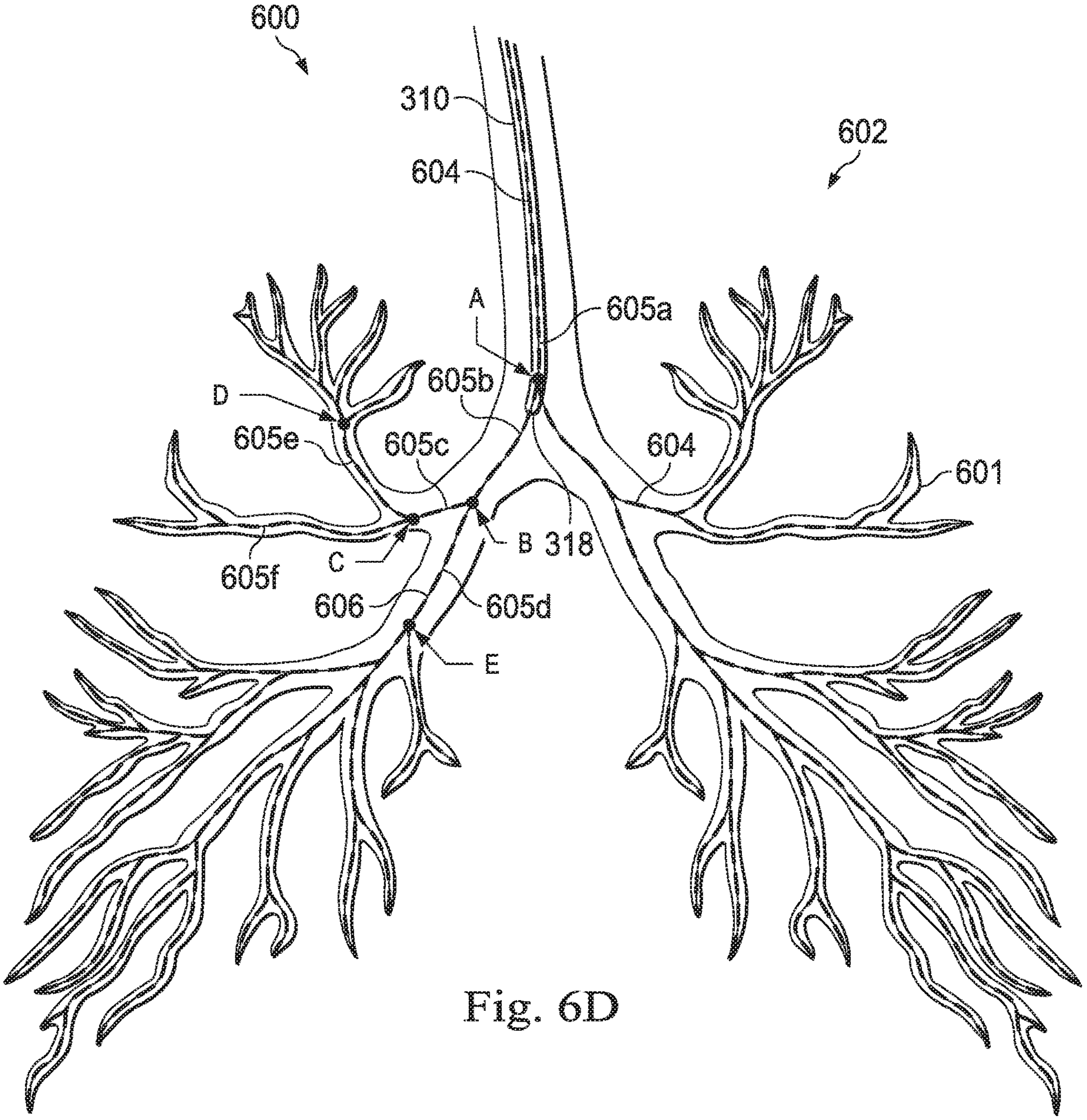
Figure 6E:
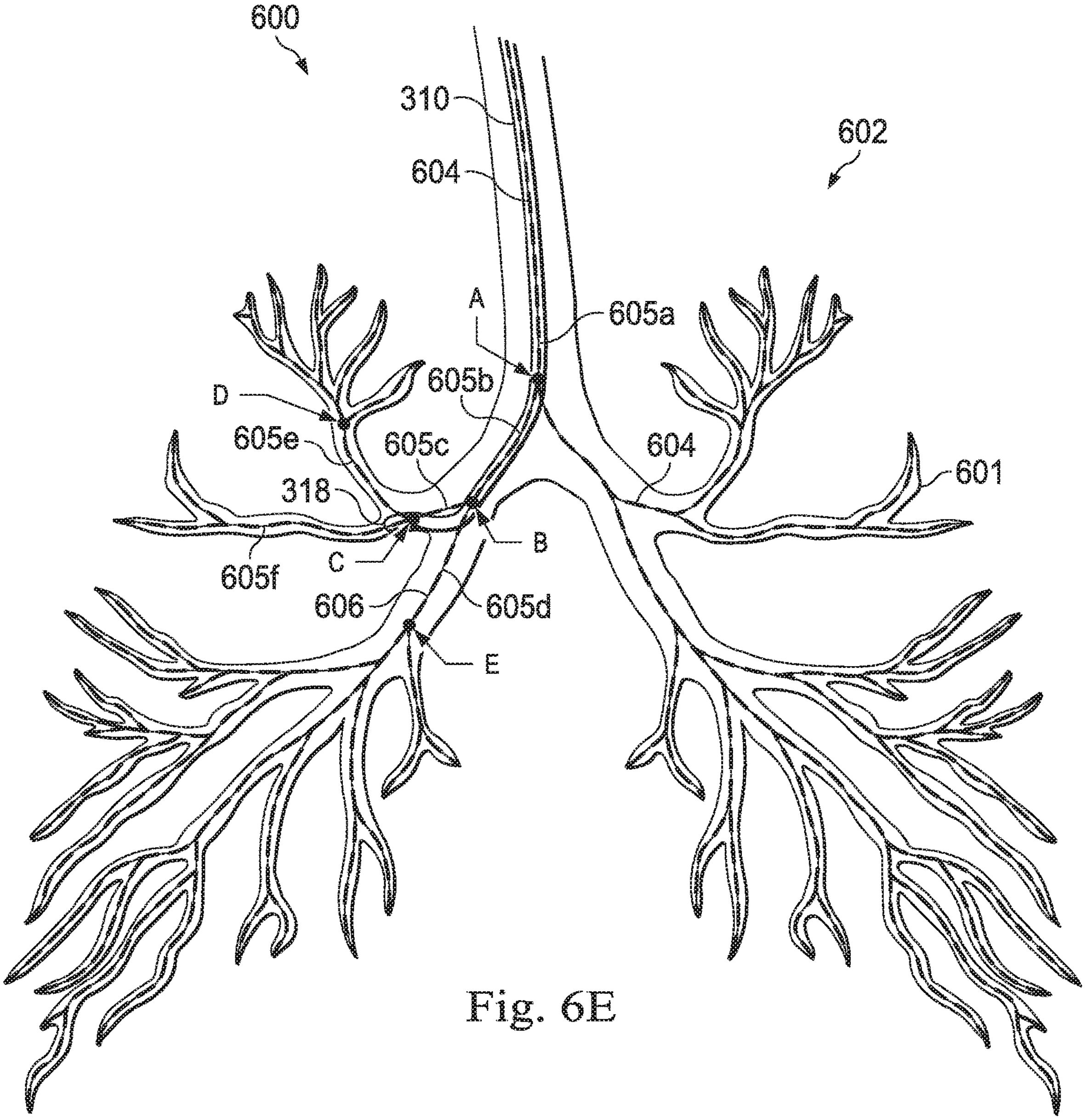
Figure 6F:
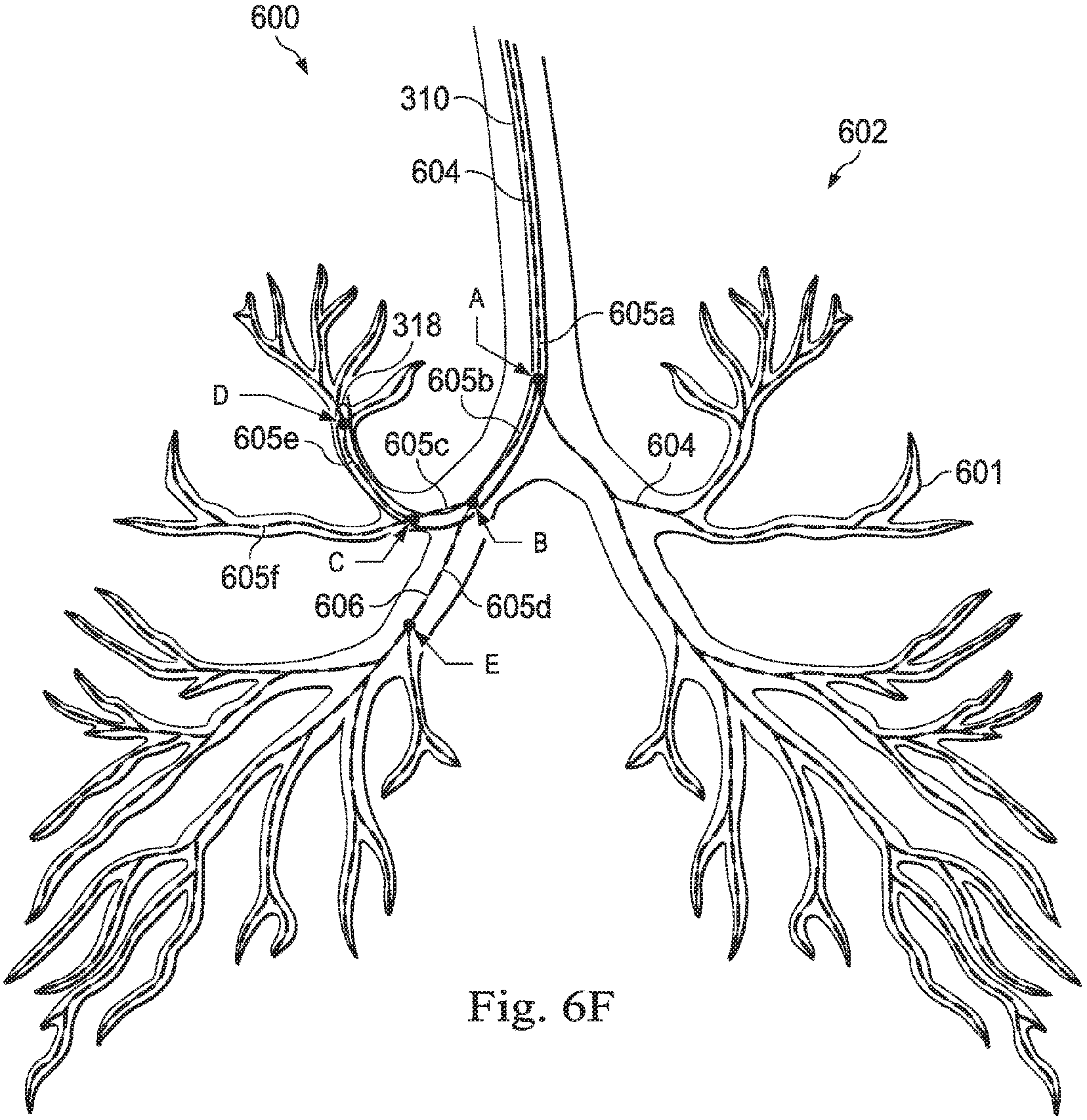
Figure 6G:
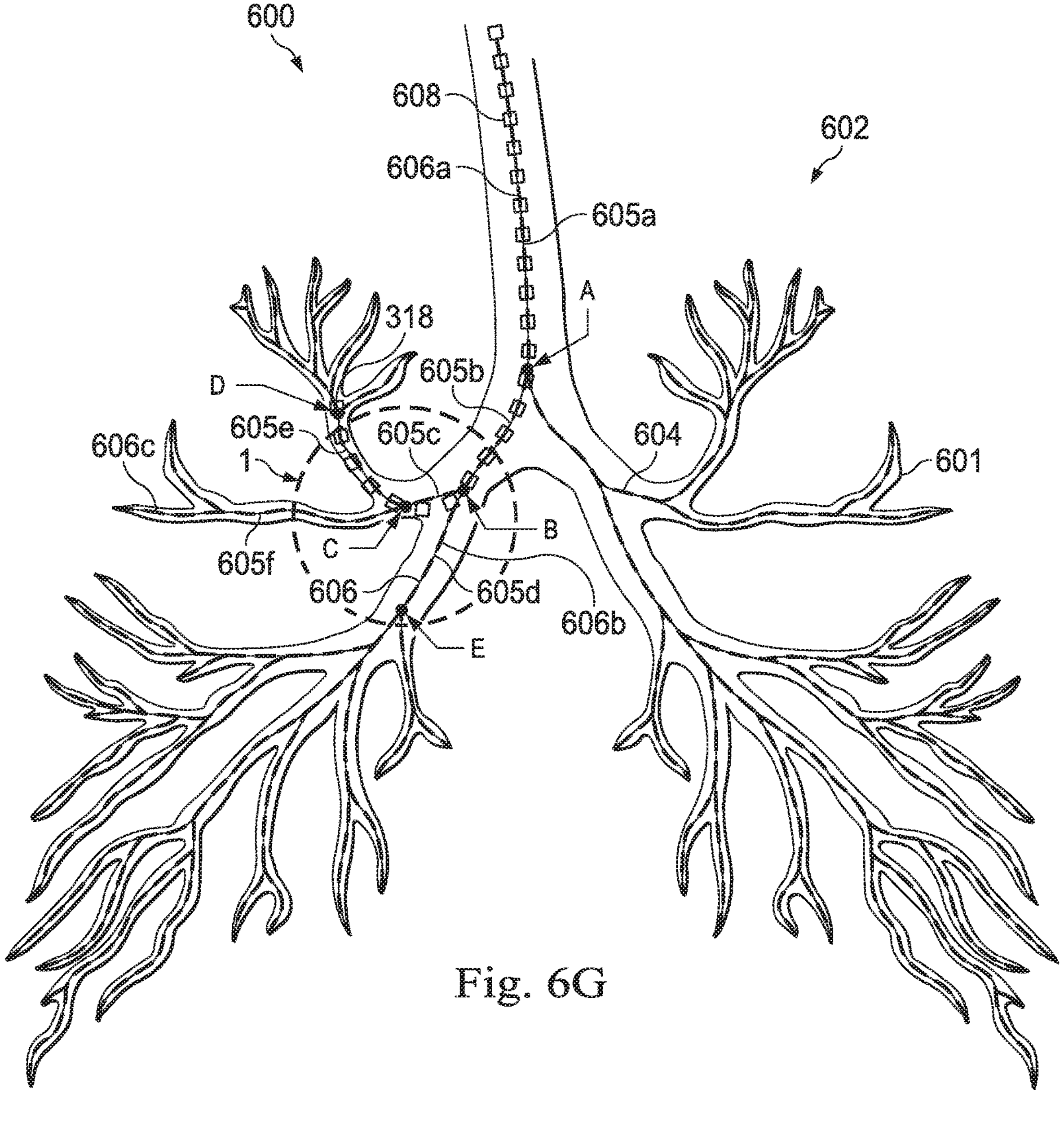
Figure 6H:
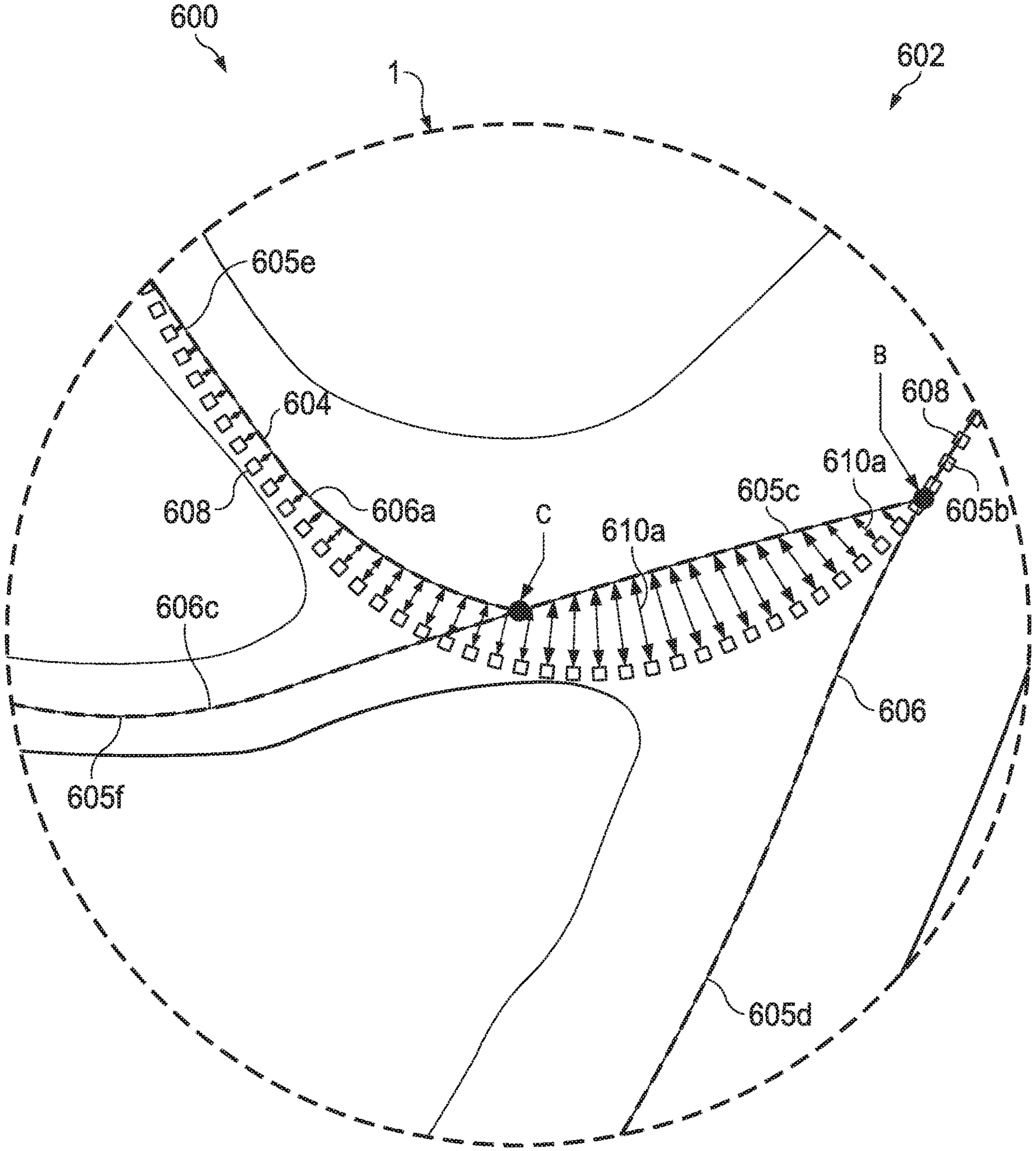
Figure 6I:
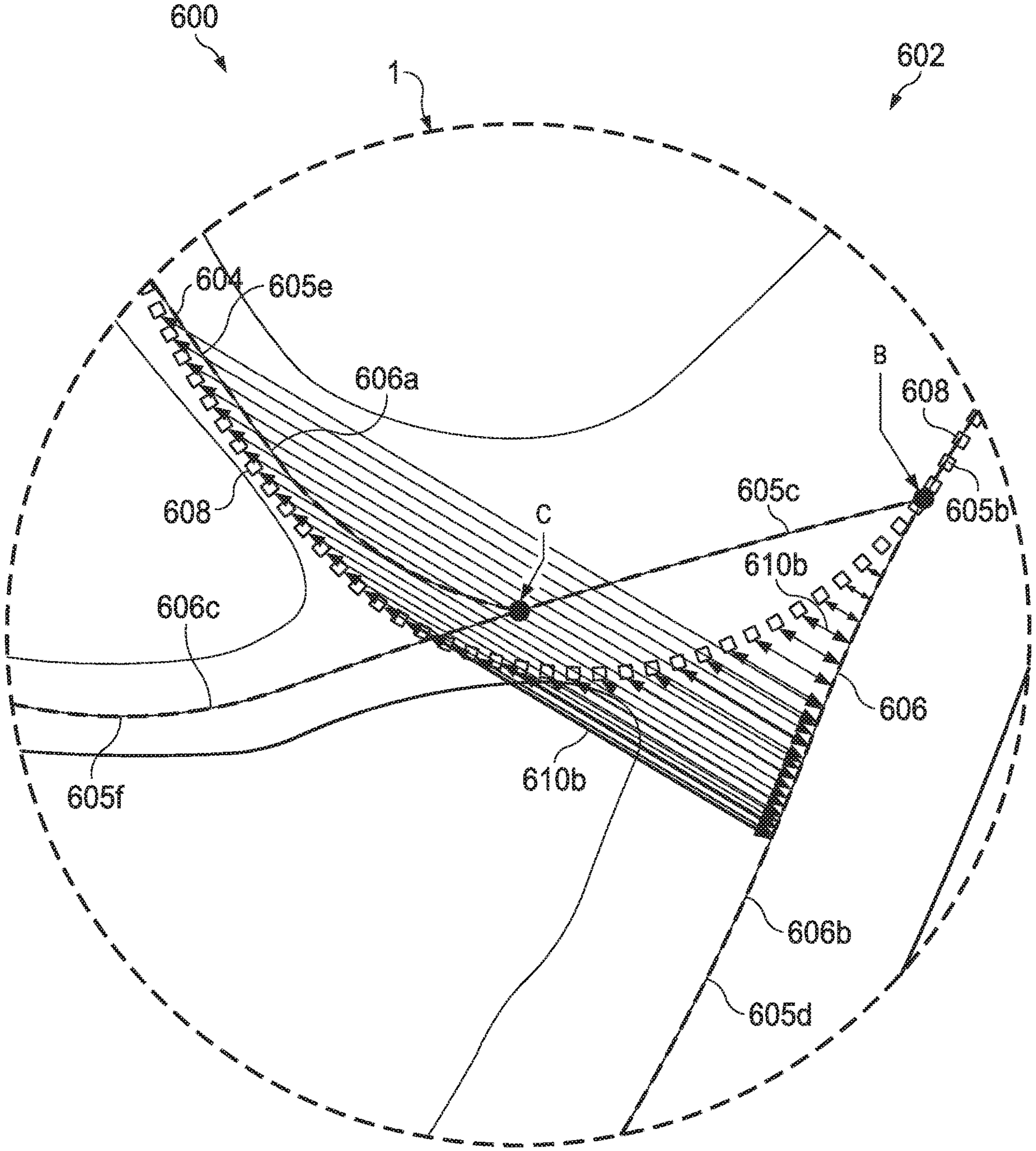
Figure 6J:
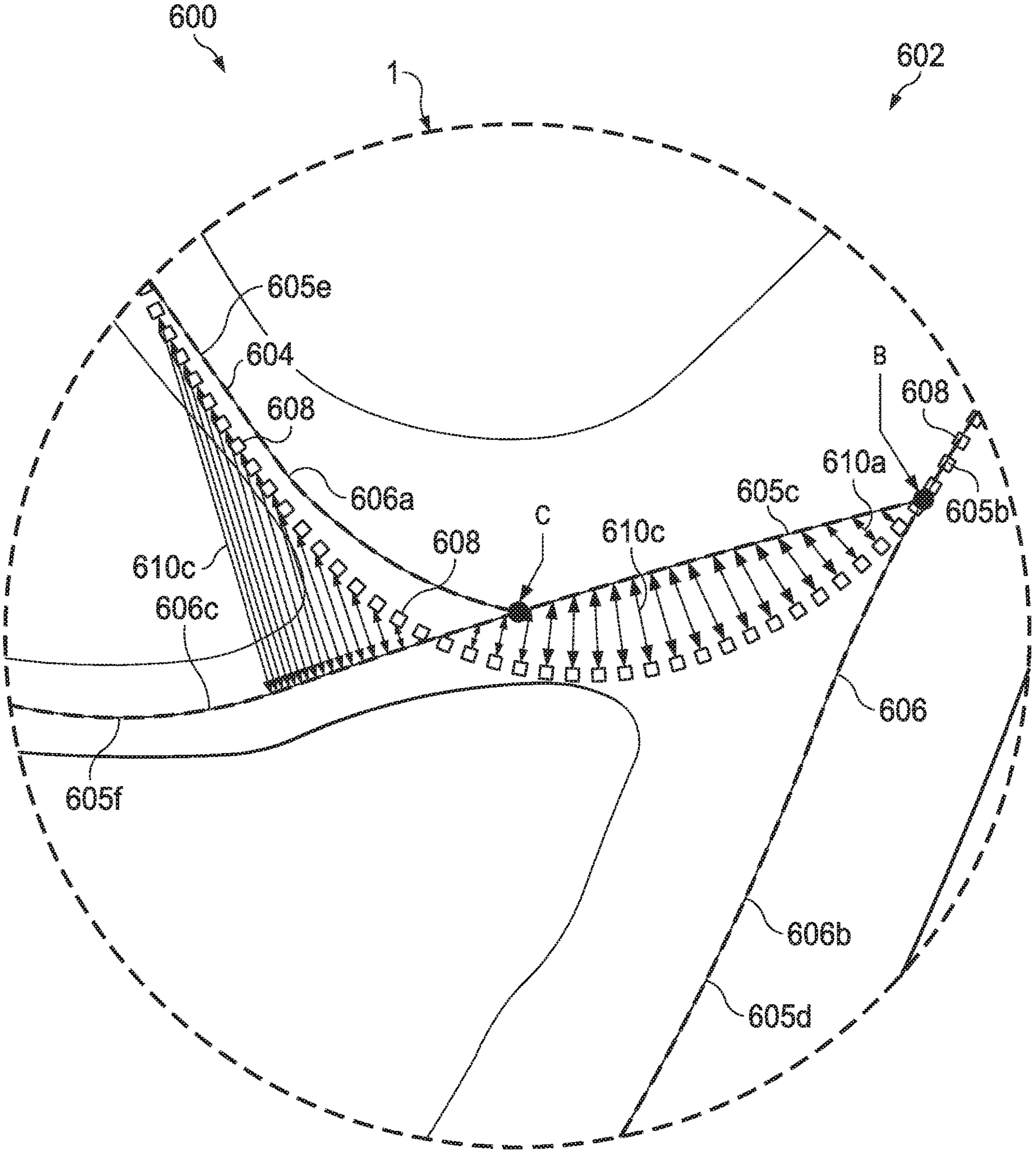

FIG. 6H-6J illustrate an enlarged view of a portion of FIG. 6G.

Figure 7:
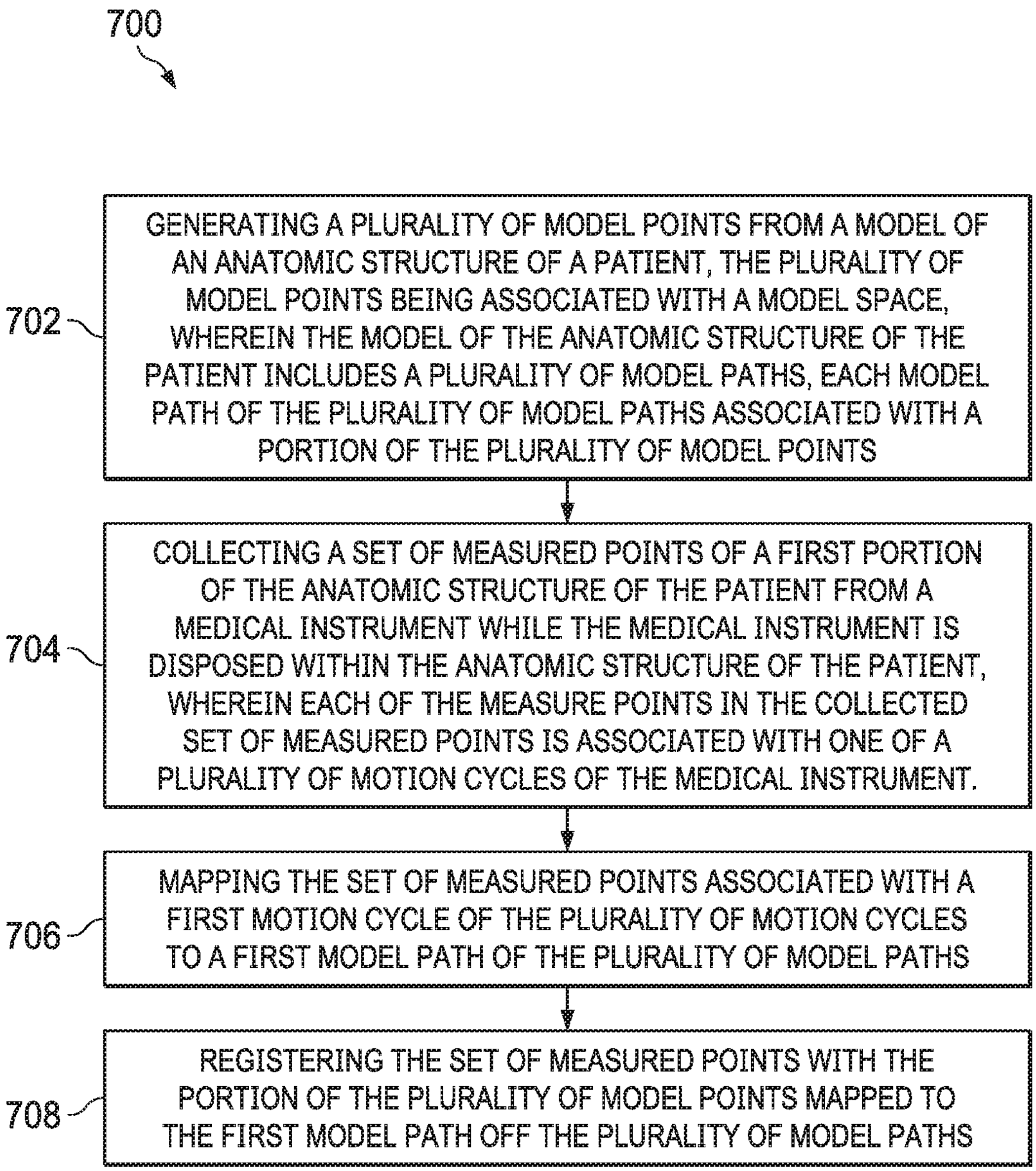

FIG. 7 is a flow chart illustrating a method for registering the model of the anatomy of the patient P to the anatomy of the patient P as-present in a surgical environment according to some embodiments.

Embodiments of the present disclosure and their advantages are best understood by referring to the detailed description that follows. It should be appreciated that like reference numerals are used to identify like elements illustrated in one or more of the figures, wherein showings therein are for purposes of illustrating embodiments of the present disclosure and not for purposes of limiting the same.

DETAILED DESCRIPTION

In the following description, specific details are set forth describing some embodiments consistent with the present disclosure. Numerous specific details are set forth in order to provide a thorough understanding of the embodiments. It will be apparent, however, to one skilled in the art that some embodiments may be practiced without some or all of these specific details. The specific embodiments disclosed herein are meant to be illustrative but not limiting. One skilled in the art may realize other elements that, although not specifically described here, are within the scope and the spirit of this disclosure. In addition, to avoid unnecessary repetition, one or more features shown and described in association with one embodiment may be incorporated into other embodiments unless specifically described otherwise or if the one or more features would make an embodiment non-functional.

Various embodiments of teleoperational medical systems including registration systems are described herein. In some embodiments, the systems may utilize a first motion cycle of a medical instrument within an anatomy of a patient, including an insertion cycle and a retraction cycle of the medical instrument as part of the registration process. In some embodiments, the first motion cycle of the medical instrument within the anatomy of the patient may include one of an insertion cycle, a retraction cycle, or a partial cycle. In some embodiments, the first motion cycle includes a discrete period of motion of the medical instrument along a direction of movement. In some embodiments, the systems may include a medical instrument including an elongate flexible body and a sensor to collect a plurality of measured points within the anatomy of the patient. In some embodiments, the systems may generate a model of the anatomy of the patient including a plurality of model points and a plurality of model paths associated with at least a portion of the model points. While some embodiments are provided herein with respect to such procedures, any reference to medical or surgical instruments and medical or surgical methods is non-limiting. In some embodiments, the systems may be used for non-teleoperational procedures involving traditional manually operated medical instruments. The systems, instruments, and methods described herein may be used for animals, human cadavers, animal cadavers, portions of human or animal anatomy, non-surgical diagnosis, as well as for industrial systems and general robotic, general teleoperational, or robotic medical systems.

Figure 1:
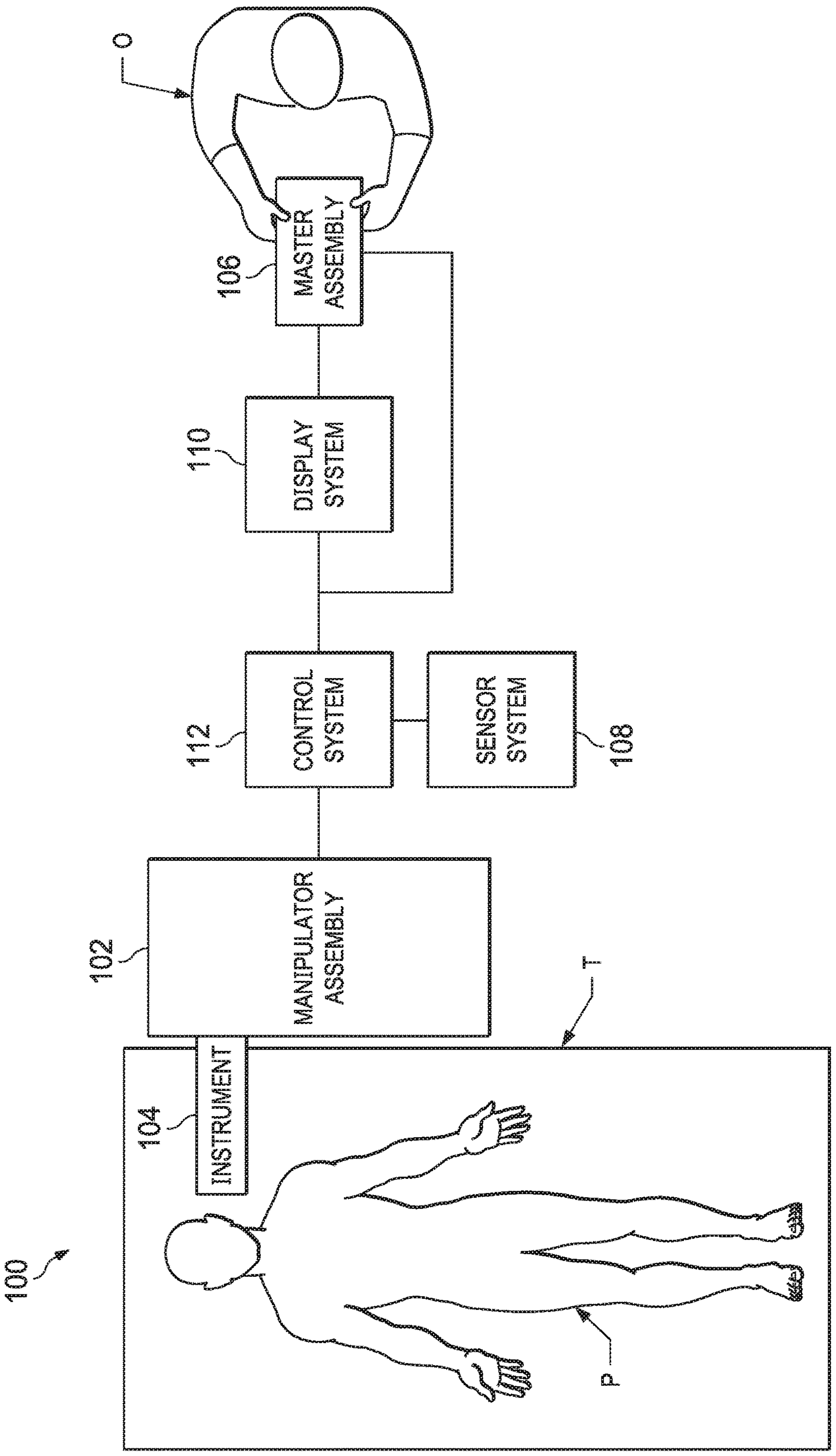
FIG. 1 is a simplified diagram of a teleoperated medical system according to some embodiments.

FIG. 1 is a simplified diagram of a teleoperated medical system 100 according to some embodiments. In some embodiments, teleoperated medical system 100 may be suitable for use in, for example, surgical, diagnostic, therapeutic, or biopsy procedures. While some embodiments are provided herein with respect to such procedures, any reference to medical or surgical instruments and medical or surgical methods is non-limiting.

As shown in FIG. 1, medical system 100 generally includes a manipulator assembly 102 for operating a medical instrument 104 in performing various procedures on a patient P. The manipulator assembly 102 may be teleoperated, non-teleoperated, or a hybrid teleoperated and non-teleoperated assembly with select degrees of freedom of motion that may be motorized and/or teleoperated and select degrees of freedom of motion that may be non-motorized and/or non-teleoperated. Manipulator assembly 102 is mounted to or near an operating table T. A master assembly 106 allows an operator (e.g., a surgeon, a clinician, or a physician as illustrated in FIG. 1) O to view the interventional site and to control manipulator assembly 102.

Master assembly 106 may be located at an operator console which is usually located in the same room as operating table T, such as at the side of a surgical table on which patient P is located. However, it should be understood that operator O can be located in a different room or a completely different building from patient P. Master assembly 106 generally includes one or more control devices for controlling manipulator assembly 102. The control devices may include any number of a variety of input devices, such as joysticks, trackballs, data gloves, trigger-guns, hand-operated controllers, voice recognition devices, body motion or presence sensors, and/or the like. To provide operator O a strong sense of directly controlling instruments 104 the control devices may be provided with the same degrees of freedom as the associated medical instrument 104. In this manner, the control devices provide operator O with telepresence or the perception that the control devices are integral with medical instruments 104.

Manipulator assembly 102 supports medical instrument 104 and may include a kinematic structure of one or more non-servo controlled links (e.g., one or more links that may be manually positioned and locked in place, generally referred to as a set-up structure), and/or one or more servo controlled links (e.g. one more links that may be controlled in response to commands from the control system), and a manipulator. Manipulator assembly 102 may optionally include a plurality of actuators or motors that drive inputs on medical instrument 104 in response to commands from the control system (e.g., a control system 112). The actuators may optionally include drive systems that when coupled to medical instrument 104 may advance medical instrument 104 into a naturally or surgically created anatomic orifice. Other drive systems may move the distal end of medical instrument 104 in multiple degrees of freedom, which may include three degrees of linear motion (e.g., linear motion along the X, Y, Z Cartesian axes) and in three degrees of rotational motion (e.g., rotation about the X, Y, Z Cartesian axes). Additionally, the actuators can be used to actuate an articulable end effector of medical instrument 104 for grasping tissue in the jaws of a biopsy device and/or the like. Actuator position sensors such as resolvers, encoders, potentiometers, and other mechanisms may provide sensor data to medical system 100 describing the rotation and orientation of the motor shafts. This position sensor data may be used to determine motion of the objects manipulated by the actuators.

Teleoperated medical system 100 may include a sensor system 108 with one or more sub-systems for receiving information about the instruments of manipulator assembly 102. Such sub-systems may include a position/location sensor system (e.g., an electromagnetic (EM) sensor system); a shape sensor system for determining the position, orientation, speed, velocity, pose, and/or shape of a distal end and/or of one or more segments along a flexible body that may make up medical instrument 104; and/or a visualization system for capturing images from the distal end of medical instrument 104.

Teleoperated medical system 100 also includes a display system 110 for displaying an image or representation of the surgical site and medical instrument 104 generated by subsystems of sensor system 108. Display system 110 and master assembly 106 may be oriented so operator O can control medical instrument 104 and master assembly 106 with the perception of telepresence.

In some embodiments, medical instrument 104 may be part of a visualization system and include a viewing scope assembly that records a concurrent or real-time image of a surgical site and provides the image to the operator or operator O through one or more displays of medical system 100, such as one or more displays of display system 110. The concurrent image may be, for example, a two or three-dimensional image captured by an endoscope positioned within the surgical site. In some embodiments, the visualization system includes endoscopic components that may be integrally or removably coupled to medical instrument 104. However, in some embodiments, a separate endoscope, attached to a separate manipulator assembly may be used with medical instrument 104 to image the surgical site. The visualization system may be implemented as hardware, firmware, software or a combination thereof which interact with or are otherwise executed by one or more computer processors, which may include the processors of a control system 112.

Display system 110 may also display an image of the surgical site and medical instruments captured by the visualization system. In some examples, teleoperated medical system 100 may configure medical instrument 104 and controls of master assembly 106 such that the relative positions of the medical instruments are similar to the relative positions of the eyes and hands of operator O. In this manner operator O can manipulate medical instrument 104 and the hand control as if viewing the workspace in substantially true presence. By true presence, it is meant that the presentation of an image is a true perspective image simulating the viewpoint of a physician that is physically manipulating medical instrument 104.

In some examples, display system 110 may present images of a surgical site recorded pre-operatively or intra-operatively using image data from imaging technology such as, computed tomography (CT), magnetic resonance imaging (MRI), fluoroscopy, thermography, ultrasound, optical coherence tomography (OCT), thermal imaging, impedance imaging, laser imaging, nanotube X-ray imaging, and/or the like. The pre-operative or intra-operative image data may be presented as two-dimensional, three-dimensional, or four-dimensional (including e.g., time based or velocity-based information) images and/or as images from models created from the pre-operative or intra-operative image data sets.

In some embodiments, often for purposes of imaged guided surgical procedures, display system 110 may display a virtual navigational image in which the actual location of medical instrument 104 is registered (i.e., dynamically referenced) with the preoperative or concurrent images/model. This may be done to present the operator O with a virtual image of the internal surgical site from a viewpoint of medical instrument 104. In some examples, the viewpoint may be from a tip of medical instrument 104. An image of the tip of medical instrument 104 and/or other graphical or alphanumeric indicators may be superimposed on the virtual image to assist operator O controlling medical instrument 104. In some examples, medical instrument 104 may not be visible in the virtual image.

In some embodiments, display system 110 may display a virtual navigational image in which the actual location of medical instrument 104 is registered with preoperative or concurrent images to present the operator O with a virtual image of medical instrument 104 within the surgical site from an external viewpoint. An image of a portion of medical instrument 104 or other graphical or alphanumeric indicators may be superimposed on the virtual image to assist operator O in the control of medical instrument 104. As described herein, visual representations of data points may be rendered to display system 110. For example, measured data points, moved data points, registered data points, and other data points described herein may be displayed on display system 110 in a visual representation. The data points may be visually represented in a user interface by a plurality of points or dots on display system 110 or as a rendered model, such as a mesh or wire model created based on the set of data points. In some examples, the data points may be color coded according to the data they represent. In some embodiments, a visual representation may be refreshed in display system 110 after each processing operation has been implemented to alter data points.

Teleoperated medical system 100 may also include control system 112. Control system 112 includes at least one memory and at least one computer processor (not shown) for effecting control between medical instrument 104, master assembly 106, sensor system 108, and display system 110. Control system 112 also includes programmed instructions (e.g., a non-transitory machine-readable medium storing the instructions) to implement some or all of the methods described in accordance with aspects disclosed herein, including instructions for providing information to display system 110. While control system 112 is shown as a single block in the simplified schematic of FIG. 1, the system may include two or more data processing circuits with one portion of the processing optionally being performed on or adjacent to manipulator assembly 102, another portion of the processing being performed at master assembly 106, and/or the like. The processors of control system 112 may execute instructions comprising instruction corresponding to processes disclosed herein and described in more detail below. Any of a wide variety of centralized or distributed data processing architectures may be employed. Similarly, the programmed instructions may be implemented as a number of separate programs or subroutines, or they may be integrated into a number of other aspects of the teleoperational systems described herein. In one embodiment, control system 112 supports wireless communication protocols such as Bluetooth, IrDA, HomeRF, IEEE 802.11, DECT, and Wireless Telemetry.

In some embodiments, control system 112 may receive force and/or torque feedback from medical instrument 104. Responsive to the feedback, control system 112 may transmit signals to master assembly 106. In some examples, control system 112 may transmit signals instructing one or more actuators of manipulator assembly 102 to move medical instrument 104. Medical instrument 104 may extend into an internal surgical site within the body of patient P via openings in the body of patient P. Any suitable conventional and/or specialized actuators may be used. In some examples, the one or more actuators may be separate from, or integrated with, manipulator assembly 102. In some embodiments, the one or more actuators and manipulator assembly 102 are provided as part of a teleoperational cart positioned adjacent to patient P and operating table T.

Control system 112 may optionally further include at least part of the virtual visualization system to provide navigation assistance to operator O when controlling medical instrument 104 during an image-guided surgical procedure. Virtual navigation using the virtual visualization system may be based upon reference to an acquired preoperative or intra-operative dataset of anatomic passageways. The virtual visualization system processes images of the surgical site imaged using imaging technology such as computerized tomography (CT), magnetic resonance imaging (MRI), fluoroscopy, thermography, ultrasound, optical coherence tomography (OCT), thermal imaging, impedance imaging, laser imaging, nanotube X-ray imaging, and/or the like. Software, which may be used in combination with manual inputs, is used to convert the recorded images into segmented two dimensional or three-dimensional composite representation of a partial or an entire anatomic organ or anatomic region. An image data set is associated with the composite representation. The composite representation and the image data set describe the various locations and shapes of the passageways and their connectivity. The images used to generate the composite representation may be recorded preoperatively or intra-operatively during a clinical procedure. In some embodiments, a virtual visualization system may use standard representations (i.e., not patient specific) or hybrids of a standard representation and patient specific data. The composite representation and any virtual images generated by the composite representation may represent the static posture of a deformable anatomic region during one or more phases of motion (e.g., during an inspiration/expiration cycle of a lung).

During a virtual navigation procedure, sensor system 108 may be used to monitor a position of the medical instrument 104 and compute an approximate location of medical instrument 104 with respect to the anatomy of patient P. The location can be used to produce both macro-level (external) tracking images of the anatomy of patient P and virtual internal images of the anatomy of patient P. The system may implement one or more electromagnetic (EM) sensor, fiber optic sensors, and/or other sensors to register and display a medical implement together with preoperatively recorded surgical images, such as those from a virtual visualization system. For example, PCT Publication WO 2016/191298 (published Dec. 1, 2016) (disclosing "Systems and Methods of Registration for Image Guided Surgery"), which is incorporated by reference herein in its entirety, discloses such one system. Teleoperated medical system 100 may further include optional operations and support systems (not shown) such as illumination systems, steering control systems, irrigation systems, and/or suction systems. In some embodiments, teleoperated medical system 100 may include more than one manipulator assembly and/or more than one master assembly. The exact number of teleoperational manipulator assemblies will depend on the surgical procedure and the space constraints within the operating room, among other factors. Master assembly 106 may be collocated or they may be positioned in separate locations. Multiple master assemblies allow more than one operator to control one or more teleoperational manipulator assemblies in various combinations.

FIG. 2A is a simplified diagram of a medical instrument system 200 according to some embodiments. In some embodiments, medical instrument system 200 may be used as medical instrument 104 in an image-guided medical procedure performed with teleoperated medical system 100. In some examples, medical instrument system 200 may be used for non-teleoperational exploratory procedures or in procedures involving traditional manually operated medical instruments, such as endoscopy. Optionally medical instrument system 200 may be used to gather (i.e., measure) a set of data points corresponding to locations within anatomic passageways of a patient, such as patient P.

Medical instrument system 200 includes elongate device 202, such as a flexible catheter, coupled to a drive unit 204. Elongate device 202 includes a flexible body 216 having proximal end 217 and distal end or tip portion 218. In some embodiments, flexible body 216 has an approximately 3 mm outer diameter. Other flexible body outer diameters may be larger or smaller.

Medical instrument system 200 further includes a tracking system 230 for determining the position, orientation, speed, velocity, pose, and/or shape of distal end 218 and/or of one or more segments 224 along flexible body 216 using one or more sensors and/or imaging devices as described in further detail below. The entire length of flexible body 216, between distal end 218 and proximal end 217, may be effectively divided into segments 224. Tracking system 230 may optionally be implemented as hardware, firmware, software or a combination thereof which interact with or are otherwise executed by one or more computer processors, which may include the processors of control system 112 in FIG. 1.

Tracking system 230 may optionally track distal end 218 and/or one or more of the segments 224 using a shape sensor 222. Shape sensor 222 may optionally include an optical fiber aligned with flexible body 216 (e.g., provided within an interior channel (not shown) or mounted externally). In one embodiment, the optical fiber has a diameter of approximately 200 μm. In other embodiments, the dimensions may be larger or smaller. The optical fiber of shape sensor 222 forms a fiber optic bend sensor for monitoring and determining the shape of flexible body 216 to generate position data. In one alternative, optical fibers including Fiber Bragg Gratings (FBGs) are used to provide strain measurements in structures in one or more dimensions. Various systems and methods for monitoring the shape and relative position of an optical fiber in three dimensions are described in U.S. patent application Ser. No. 11/180,389 (filed Jul. 13, 2005) (disclosing "Fiber optic position and shape sensing device and method relating thereto"); U.S. patent application Ser. No. 12/047,056 (filed on Jul. 16, 2004) (disclosing "Fiber-optic shape and relative position sensing"); and U.S. Pat. No. 6,389,187 (filed on Jun. 17, 1998) (disclosing "Optical Fibre Bend Sensor"), which are all incorporated by reference herein in their entireties. Sensors in some embodiments may employ other suitable strain sensing techniques, such as Rayleigh scattering, Raman scattering, Brillouin scattering, and Fluorescence scattering. In some embodiments, the shape of the elongate device may be determined using other techniques. For example, a history of the distal end pose of flexible body 216 can be used to reconstruct the shape of flexible body 216 over the interval of time. In some embodiments, tracking system 230 may optionally and/or additionally track distal end 218 using a position sensor system 220, such as an electromagnetic (EM) sensor system.

Flexible body 216 includes a channel 221 sized and shaped to receive a medical instrument 226. FIG. 2B is a simplified diagram of flexible body 216 with medical instrument 226 extended according to some embodiments. In some embodiments, medical instrument 226 may be used for procedures such as surgery, biopsy, ablation, illumination, irrigation, or suction. Medical instrument 226 can be deployed through channel 221 of flexible body 216 and used at a target location within the anatomy. Medical instrument 226 may include, for example, image capture probes, biopsy instruments, laser ablation fibers, and/or other surgical, diagnostic, or therapeutic tools. Medical tools may include end effectors having a single working member such as a scalpel, a blunt blade, an optical fiber, an electrode, and/or the like. Other end effectors may include, for example, forceps, graspers, scissors, clip appliers, and/or the like. Other end effectors may further include electrically activated end effectors such as electrosurgical electrodes, transducers, sensors, and/or the like. Medical instrument 226 may be advanced from the opening of channel 221 to perform the procedure and then retracted back into the channel when the procedure is complete. Medical instrument 226 may be removed from proximal end 217 of flexible body 216 or from another optional instrument port (not shown) along flexible body 216.

Medical instrument 226 may additionally house cables, linkages, or other actuation controls (not shown) that extend between its proximal and distal ends to controllably the bend distal end of medical instrument 226. Steerable instruments are described in detail in U.S. Pat. No. 7,316,681 (filed on Oct. 4, 2005) (disclosing "Articulated Surgical Instrument for Performing Minimally Invasive Surgery with Enhanced Dexterity and Sensitivity") and U.S. patent application Ser. No. 12/286,644 (filed Sep. 30, 2008) (disclosing "Passive Preload and Capstan Drive for Surgical Instruments"), which are incorporated by reference herein in their entireties.

Flexible body 216 may also house cables, linkages, or other steering controls (not shown) that extend between drive unit 204 and distal end 218 to controllably bend distal end 218 as shown, for example, by broken dashed line depictions 219 of distal end 218. In some examples, at least four cables are used to provide independent "up-down" steering to control a pitch of distal end 218 and "left-right" steering to control a yaw of distal end 281. Steerable elongate devices are described in detail in U.S. patent application Ser. No. 13/274,208 (filed Oct. 14, 2011) (disclosing "Catheter with Removable Vision Probe"), which is incorporated by reference herein in its entirety. In embodiments in which medical instrument system 200 is actuated by a teleoperational assembly, drive unit 204 may include drive inputs that removably couple to and receive power from drive elements, such as actuators, of the teleoperational assembly. In some embodiments, medical instrument system 200 may include gripping features, manual actuators, or other components for manually controlling the motion of medical instrument system 200.

In some embodiments, medical instrument system 200 may include a flexible bronchial instrument, such as a bronchoscope or bronchial catheter, for use in examination, diagnosis, biopsy, or treatment of a lung. Medical instrument system 200 is also suited for navigation and treatment of other tissues, via natural or surgically created connected passageways, in any of a variety of anatomic systems, including the colon, the intestines, the kidneys and kidney calices, the brain, the heart, the circulatory system including vasculature, and/or the like.

The information from tracking system 230 may be sent to a navigation system 232 where it is combined with information from visualization system 231 and/or the preoperatively obtained models to provide the physician or other operator with real-time position information. In some examples, the real-time position information may be displayed on display system 110 of FIG. 1 for use in the control of medical instrument system 200. In some examples, control system 116 of FIG. 1 may utilize the position information as feedback for positioning medical instrument system 200. Various systems for using fiber optic sensors to register and display a surgical instrument with surgical images are provided in U.S. patent application Ser. No. 13/107,562, filed May 13, 2011, disclosing, "Medical System Providing Dynamic Registration of a Model of an Anatomic Structure for Image-Guided Surgery," PCT Publication WO 2016/1033596 (filed May 20, 2016) (disclosing "Systems and Methods of Registration for Image Guided Surgery"), and PCT Publication WO 2016/164311 (filed Apr. 4, 2016) (disclosing "Systems and Methods of Registration Compensation in Image Guided Surgery"), which are incorporated by reference herein in their entirety.

FIGS. 3A and 3B are simplified diagrams of side views of a patient coordinate space (or "instrument space") including a medical instrument mounted on an insertion assembly according to some embodiments. Known points within the patient coordinate space may include coordinates such as a set of $X_I$, $Y_I$, and $Z_I$ coordinates. As shown in FIGS. 3A and 3B, a surgical environment 300 includes a patient P that is positioned on the table T of FIG. 1. Patient P may be stationary within the surgical environment in the sense that gross patient movement is limited by sedation, restraint, and/or other means. Cyclic anatomic motion including respiration and cardiac motion of patient P may continue, unless patient is asked to hold his or her breath to temporarily suspend respiratory motion. Accordingly, in some embodiments, data may be gathered at a specific phase in respiration and filtered such that the data is tagged and identified with that phase. In some embodiments, the phase during which data is collected may be inferred from physiological information collected from patient P. Within surgical environment 300, a point gathering instrument 304 is coupled to an instrument carriage 306. In some embodiments, the point gathering instrument 304 may include components of the medical system 200 including, for example, the elongate device 202 and the drive unit 204. In some embodiments, point gathering instrument 304 may use EM sensors, shape-sensors, and/or other sensor modalities. Instrument carriage 306 is mounted to an insertion stage 308 fixed within surgical environment 300. Alternatively, insertion stage 308 may be movable but have a known location (e.g., via a tracking sensor or other tracking device) within surgical environment 300. Instrument carriage 306 may be a component of a manipulator assembly (e.g., manipulator assembly 102) that couples to point gathering instrument 304 to control insertion motion (i.e., motion along the A axis) and, optionally, motion of a distal end 318 of an elongate device 310, or medical instrument, in multiple directions including yaw, pitch, and roll. Instrument carriage 306 or insertion stage 308 may include actuators, such as servomotors, (not shown) that control motion of instrument carriage 306 along insertion stage 308.

Elongate device 310 is coupled to an instrument body 312. Instrument body 312 is coupled and fixed relative to instrument carriage 306. In some embodiments, an optical fiber shape sensor 314 is fixed at a proximal point 316 on instrument body 312. In some embodiments, proximal point 316 of optical fiber shape sensor 314 may be movable along with instrument body 312 but the location of proximal point 316 may be known (e.g., via a tracking sensor or other tracking device). Shape sensor 314 measures a shape from proximal point 316 to another point such as distal end 318 of elongate device 310. Point gathering instrument 304 may be substantially similar to medical instrument system 200.

A position measuring device 320 provides information about the position of instrument body 312 as it moves on insertion stage 308 along an insertion axis A. Position measuring device 320 may include resolvers, encoders, potentiometers, and/or other sensors that determine the rotation and/or orientation of the actuators controlling the motion of instrument carriage 306 and consequently the motion of instrument body 312. In some embodiments, insertion stage 308 is linear. In some embodiments, insertion stage 308 may be curved or have a combination of curved and linear sections.

FIG. 3A shows instrument body 312 and instrument carriage 306 in a retracted position along insertion stage 308. In this retracted position, proximal point 316 is at a position L0 on axis A. In this position along insertion stage 308 an A component of the location of proximal point 316 may be set to a zero and/or another reference value to provide a base reference to describe the position of instrument carriage 306, and thus proximal point 316, on insertion stage 308. With this retracted position of instrument body 312 and instrument carriage 306, distal end 318 of elongate device 310 may be positioned just inside an entry orifice of patient P. Also, in this position, position measuring device 320 may be set to a zero and/or the other reference value (e.g., I=0). In FIG. 3B, instrument body 312 and instrument carriage 306 have advanced along the linear track of insertion stage 308 and distal end 318 of elongate device 310 has advanced into patient P. In this advanced position, the proximal point 316 is at a position L1 on the axis A. In this embodiment, a motion cycle of the elongate device 310 is defined as a single insertion of the elongate device 310 from a starting point within an entry orifice of the patient P to an end point further advanced into the anatomy of the patient P and a corresponding single retraction of the elongate device 310 from the end point to the starting point lying within the entry orifice of the patient P. The corresponding single retraction typically occurs immediately after the single insertion such that it can be deduced the location of the starting point of the retraction within the patient anatomy is identical to the location of the ending point of the insertion. Additionally, a plurality of motion cycles of the elongate device 310 may be completed during a procedure such as those that have been described above. In some examples, encoder and/or other position data from one or more actuators controlling movement of instrument carriage 306 along insertion stage 308 and/or one or more position sensors associated with instrument carriage 306 and/or insertion stage 308 is used to determine the position $L_X$ of proximal point 316 relative to position $L_0$. In some examples, position $L_X$ may further be used as an indicator of the distance or insertion depth to which distal end 318 of elongate device 310 is inserted into the passageways of the anatomy of patient P.

FIGS. 4A, 4B, 4C, and 4D illustrate the advancement of elongate device 310 of FIGS. 3A and 3B through anatomic passageways 402 of the lungs 400 of the patient P of FIGS. 1 and 3A and 3B. These anatomic passageways 402 include the trachea and the bronchial tubes. As the elongate device 310 is advanced with the instrument carriage 306 moving along the insertion stage 308, the operator O may steer the distal end 318 of elongate device 310 to navigate through the anatomic passageways 402. In navigating through the anatomic passageways 402, elongate device 310 assumes a shape that may be measured by the shape sensor 314 extending within the elongate device 310.

FIG. 5 is a flowchart illustrating a general method 500 for use in an image-guided surgical procedure. The method 500 is illustrated in FIG. 5 as a set of operations or processes 502 through 510. Not all of the illustrated processes 502 through 510 may be performed in all embodiments of method 500. Additionally, one or more processes that are not expressly illustrated in FIG. 5 may be included before, after, in between, or as part of the processes 502 through 510. In some embodiments, one or more of the processes may be implemented, at least in part, in the form of executable code stored on non-transitory, tangible, machine-readable media that when run by one or more processors (e.g., the processors of control system 112) may cause the one or more processors to perform one or more of the processes.

At a process 502, pre-operative or intra-operative image data is obtained from imaging technology such as, computed tomography (CT), magnetic resonance imaging (MRI), fluoroscopy, thermography, ultrasound, optical coherence tomography (OCT), thermal imaging, impedance imaging, laser imaging, or nanotube X-ray imaging. The pre-operative or intra-operative image data may correspond to two-dimensional, three-dimensional, or four-dimensional (including e.g., time-based or velocity-based information) images. For example, the image data may represent the human lungs 400 of FIGS. 4A-4D.

At a process 504, a computer system either operating alone or in combination with manual input is used to convert the recorded images into a segmented two-dimensional or three-dimensional composite representation or model of a partial or an entire anatomic organ or anatomic region. For example, FIG. 6A illustrates a segmented model 600 of the lungs 400 of FIGS. 4A-4D. Due to limitations in either the data or segmentation algorithm, the segmented model 600 may not include all of the passageways of interest present within the human lungs but includes at least some passageways 601. For example, relatively narrow and/or distal passageways 601 of the lungs may not be fully included in the segmented model 600. The segmented model 600 may be a three-dimensional model, such as a mesh model, linkage model, or another suitable model defining the interior lumens or passageways 601 of the lungs of the patient P. In general, the segmented model 600 serves as a spatial template of the airway geometry within the pre-operative or intra-operative reference frame (e.g., model space). The composite representation and the image data set describe the various locations and shapes of the passageways 601 and their connectivity and may omit undesired portions of the anatomy included in the pre-operative or intra-operative image data. In some embodiments, the model 600 may include specifically desired features, such as a suspected tumor, lesion, or other tissue portion of interest.

In one example, during the segmentation process the images may be partitioned into segments or elements (e.g., pixels or voxels) that share certain characteristics or computed properties such as color, density, intensity, and texture. This segmentation process results in a two- or three-dimensional reconstruction that forms a model of the target anatomy based on the obtained image, like the model 600. To represent the model, the segmentation process may delineate sets of voxels representing the target anatomy and then apply a function, such as marching cube function, to generate a 3D surface that encloses the voxels. The model may be made by generating a mesh, volume, or voxel map. This model may be shown in the display system 110 to aid the operator O in visualizing the anatomy, such as the interior passageways 601 of the lungs.

Additionally, or alternatively, the computer system either operating alone or in combination with manual input generates a plurality of model points 604 associated with the model 600, which are represented by the dashed lines of FIG. 6B. The model points 604 can be selected manually or automatically to represent a centerline segmented model 602 during a registration process. In this regard, the model 600 may be used to generate model points 604 and, in turn, the model points 604 may be used to generate the centerline segmented model 602. The centerline segmented model 602 includes model links 605 and model paths 606, each of which may include a plurality of model links 605. The model 600, centerline segmented model 602, and model points 604 are all associated with (e.g., disposed in or referenced to) the model space. For example, each of the model points 604 of the plurality of model points 604 may include coordinates such as a set of $X_M$, $Y_M$, and $Z_M$ coordinates, or other coordinates that identify the location of each model point 604 in the three-dimensional model space. In some embodiments, each of the model points 604 may include a generation identifier that identifies which passageway 601 generation the model points 604 are associated with and/or a diameter or radius value associated with that portion of the centerline segmented model 602. In some embodiments, information describing the radius or diameter associated with a given model point 604 may be provided as part of a separate data set.

Additionally, or alternatively, as shown in FIG. 6C, the computer system may generate a plurality of model paths 606, each model path 606 of the plurality of model paths 606 being associated with a corresponding portion of the plurality of model points 604, shown in FIG. 6C. In the example illustrated in FIG. 6C. The centerline segmented model 602 may include a plurality of three-dimensional straight lines, a plurality of curved lines, or a combination of both defining the plurality of model paths 606 associated with at least a portion of the model points 604 and corresponding to the approximate center of the passageways 601 contained in the centerline segmented model 602. The higher the resolution of the model, the more accurately the set of straight or curved lines will correspond to the center of the passageways 601. In some embodiments, the plurality of model paths 606 may be associated with some other position or functional purpose within the centerline segmented model 602 to facilitate registration and data gathering within the anatomy of the patient P. Representing the lungs with the centerline segmented model 602 may provide a smaller set of data that is more efficiently processed by one or more processors or processing cores than the data set of the centerline segmented model 602, which represents the walls of the passageways 601 of the model 600. In this way the functioning of the control system 112 may be improved.

As shown in FIG. 6C, the centerline segmented model 602 includes a plurality of branch points. The branch points A, B, C, D, and E are shown at each of several of the branch points. A plurality of model links 605 are illustrated as extending within the centerline segmented model between respective branch points A, B, C, D, and E. Each model path 606 may include a plurality of model links 605, the plurality of model links 605 extending end-to-end in a series relationship with each other and each including a plurality of model points 604. In some embodiments, at least some of the model links 605 extend from points along at least one of the model paths 606 that do not correspond to a branch point. The branch point A may represent the point in the centerline segmented model 602 at which the trachea divides into the left and the right principal bronchi and the point at which a first model link 605*a* ends and a second, adjoining model link 605*b* begins. The right principal bronchus may be identified in the centerline segmented model 602 as being located between branch A and B along the second model link 605*b*. Similarly, secondary bronchi are identified by the branch point B, at the end of the second model link 605*b* and the beginning of a third model link 605*c*, and the branch point C, at the end of the third model link 605*c*. Secondary bronchi are also identified between the branch point B and the branch point E, along a fourth model link 605*d*. Another, fifth model link 605*e* may be defined between the branch points C and D. Additionally, a sixth model link 605*f* may defined as extending away from the branch point C. Each of the model paths 606 and each of the model links 605 may also be associated with a representation of a diameter of a corresponding lumen of a corresponding passageway 601 within the patient's anatomy P. In some embodiments, the centerline segmented model 602 may include an average diameter value for each of the model paths 606 and each of the model links 605. The average diameter value may be a patient-specific value, or a more general value derived from multiple patients.

After the centerline segmented model 602 is generated and stored in data as the plurality of model points 604, the plurality of model links 605, and the plurality of model paths 606 as shown in FIG. 6C, the plurality of model points 604, the plurality of model links 605, and the plurality of model paths 606 may be retrieved from data storage for use in an image-guided surgical procedure. In order to use the centerline segmented model 602 and the model 600 in the image-guided surgical procedure, the model points 604, and the corresponding model links 605 and model paths 606, may be mapped to the plurality of measured points by comparing a spatial relationship between the measured points 608 and the model points 604 (or model links 605 or model paths 606). The model points 604 may also be registered with the plurality of measured points 608 (or model links 605 or model paths 606) to associate the modeled passageways 601 in the model 600 with the patient's actual anatomy as present in a surgical environment. The mapping and registering may be performed as a function of translating or associating coordinates in the model space ($X_M$, $Y_M$, $Z_M$) to corresponding coordinates in the patient coordinate space ($X_I$, $Y_I$, $Z_I$).

FIGS. 6D-6F illustrate the advancement of elongate device 310 of FIGS. 3A and 3B through anatomic passageways 402 of lungs 400 of the patient P of FIGS. 1 and 3A and 3B relative to the centerline segmented model 602, the model points 604, the model links 605, and the model paths 606 of FIGS. 6C-6J, defining a first motion cycle. FIG. 6G illustrates the plurality of measured points 608 generated and collected by advancing the elongate device 310 within the anatomy of the patient P as shown in FIGS. 6D-6F relative to the model paths 606 as part of the first motion cycle. FIGS. 6H-6J illustrates a section 1 of FIG. 6G illustrating the plurality of measured points 608 measured during the first motion cycle relative to the model points 604 associated with the model paths 606. In FIG. 6D, the elongate device 310 has been advanced into the trachea of the patient P, approximately following the first model link 605*a* to the branch point A. In FIG. 6E, the elongate device 310 has been advanced further into the anatomy of the patient P, most closely following the second model link 605*b* and the third model link 605*c*, passing the branch point B with the distal end 318 of the elongate device 310 being positioned most closely to the branch point C. In FIG. 6F, the elongate device 310 has been advanced past the branch point C approximately following the fifth model link 605*e* past the branch point D.

Returning to FIG. 5, at a process 506, measured points 608 may be obtained from the patient anatomy P that correspond to the anatomical model, as described with reference to FIGS. 3A-B, 4A-D, and 6D-F. As illustrated in FIGS. 6D-6J, the measured points 608 (as shown in FIGS. 6G-6J) for the first motion cycle may be generated by advancing the elongate device 310 through the anatomy of the patient P and/or to landmarks in the anatomy, while measuring the position of the distal end 318 of the elongate device 310, or by measuring a pose of the elongate device 310 using a sensor system (e.g., the sensor system 108), before retracting the elongate device 310 from the patient anatomy P. In the example embodiment, the sensor system 108 includes the elongate device 310, which may include a sensor.

In some embodiments, the sensor may be an electromagnetic sensor coupled to the elongate device 310. In other embodiments, the sensor may be a shape sensor configured to generate shape observations for at least a portion of the elongate device 310. In the example embodiment, the measured points 608 are associated with one motion cycle of the elongate device 310. In some other embodiments, the measured points 608 may be associated with any number of motion cycles of the elongate device 310 that facilitates operation of the medical instrument system 200 as described herein. The measured points 608 are associated with a patient space within the anatomy of the patient P and may also be referred to as patient space points.

At a process 508, the collected set of measured points 608 associated with the first motion cycle are mapped to at least one model path 606 including a plurality of model links 605. As illustrated in FIG. 6G, the collected set of measured points 608 are mapped, or associated with the model links 605*a*, 605*b*, 605*c*, and 605*e* based on a path followed by the elongate device 310 during the first motion cycle. More specifically, the entirety of the path followed by the elongate device 310 during the first motion cycle is considered when evaluating the model paths 606, including a plurality of model links 605 connected in series, to which each of the measured points 608 should be matched. Matching measured points 608 to a model path 606 occurs as a result of identifying which of the model paths 606 the measured points 608 most closely correspond.

For example, as illustrated in FIG. 6G, a first model path 606*a* most closely aligned with the path followed by the elongate device 310 during the first motion cycle includes the first model link 605*a*, the second model link 605*b*, the third model link 605*c*, and the fifth model link 605*e*. A second model path 606*b* includes the first model link 605*a*, the second model link 605*b*, and the fourth model link 605*d*, each of the model links 605 in an end-to-end series relationship. A third model path 606*c* includes the first model link 605*a*, the second model link 605*b*, the third model link 605*c*, and the sixth model link 605*f*, each of the model links 605 in an end-to-end series relationship. In some embodiments, a plurality of model paths 606 may be considered when matching the measured points 608 to at least one of the model paths 606. In some embodiments, each model path 606 of the plurality of model paths 606 is considered when evaluating which model path 606 to match the measured points 608 to. In some other embodiments, any model path 606 within a predetermined distance of any of the measured points 608 is considered when evaluating which model path 606 to match the measured points 608 to. In some additional embodiments, each of the model paths 606 is populated with a plurality of model links 605 using the model links 605 including model points 604 that are closest to the measured points 608.

More specifically, as shown in FIGS. 6H-6J, each of the measured points 608 associated with the first motion cycle are positioned relative to the model links 605 and the model paths 606. The measured points 608 are positioned relative to the model paths 606 and the model links 605 by a distance varying from approximately overlying at least one of the model links 605 and the model paths 606, to spaced apart from at least one of the model links 605 and the model paths 606 by a measured point offset distance. With reference to FIG. 6H, a first portion of the measured points 608 are each spaced apart from the first model path 606*a* by a first offset distance 610*a*. The cumulative total of the first offset distances 610*a* for each of the measured points 608 that are not positioned along the first model path 606*a* equal a first cumulative offset value.

With reference to FIG. 6I, each of the measured points 608 of the first portion of the measured points 608 are spaced apart from the second model path 606*b* by a second offset distance 610*b*. The cumulative total of the second offset distances 610*b* for each of the measured points 608 that are not positioned along the second model path 606*b* equal a second cumulative offset value. As shown in FIG. 6J, each of the measured points 608 of the first portion of the measured points 608 are spaced apart from the third model path 606*c* by a third offset distance 610*c*. The cumulative total of the third offset distances 610*c* for each of the measured points 608 that are not positioned along the third model path 606*c* equals a third cumulative offset value. In the example shown in FIGS. 6H-6J, the first cumulative offset value is lesser than either of the second offset value and the third offset value. Therefore, it can be determined that the model path 606 most closely corresponding to the path followed by the elongate device 310 when the measured points 608 were gathered, and therefore the model path 606 associated with the measured points 608, is the model path 606 having the smallest cumulative offset value. In this embodiment, the model path 606 having the smallest cumulative offset value is the first model path 606*a*.

In the present example, based on the smallest cumulative offset value (the first cumulative offset value associated with the measured points 608 and the first model path 606*a*) and the association of the measured points 608 with the first motion cycle, all of the measured points 608 associated with the first motion cycle are mapped to the first model path 606*a*. In the example embodiment, individual measured points may be positioned relatively closer to one of the second model path 606*b* and the third model path 606*c* than the first model path 606*a*. However, to determine the model path 606 with which the measured points 608 are to be mapped, the cumulative offset value for all of the measured points 608 is determined, reducing mapping of measured points 608 to non-associated model paths 606.

At a process 510, the anatomic model data in a model space is registered to the patient coordinate space (or vice versa) prior to and/or during the course of an image-guided surgical procedure on the anatomy of patient P in the patient coordinate space. Generally, registration involves the matching of the measured points 608 with model points 604 that are associated with the model links 605 of the model path 606 to which the measured points 608 have been mapped with the least cumulative total through the use of rigid and/or non-rigid transforms. A point set registration method (e.g., iterative closes point (ICP) technique) may also be used in registration processes within the scope of this disclosure. Such a point set registration method may generate a transformation that aligns the measured points 608 (such as the set of measured points 608 obtained during one motion cycle of the elongate device 310) and the model points 604 (also referred to as a model point set) that are associated with one of the model paths 606 to which the measured points 608 have been mapped.

In various examples the resulting quality of the registration of the measured points 608 to the model points 604 associated with the model path 606 to which the measured points 608 have been mapped may depend on various factors. The factors may include for example, the numbers of the measured points 608 and/or the number of the model points 604, the density of the measured points 608 and/or the model points 604, the distribution of the measured points 608 and/or the model points 604 relative to a region of interest within the anatomy of the patient P, measurement errors associated with the measured points 608 and/or the model points 604, and deformation of the anatomy of the patient P associated with the measured points 608 and/or the model points 604.

FIG. 7 illustrates a method 700 according to some embodiments. The method 700 is illustrated as a set of operations or processes. Not all of the illustrated processes may be performed in all embodiments of method 700. Additionally, one or more processes that are not expressly illustrated in FIG. 7 may be included before, after, in between, or as part of the processes. In some embodiments, one or more of the processes may be implemented, at least in part, in the form of executable code stored on non-transitory, tangible, machine-readable media that when run by one or more processors (e.g., the processors of a control system) may cause the one or more processors to perform one or more of the processes. In one or more embodiments, the processes may be performed by a control system (e.g., control system 112).

At process 702 and with reference to FIGS. 6A and 6B, a plurality of model points 604 of a model 600 of an anatomic structure of a patient P are generated. As shown in FIG. 6C, the plurality of model points 604 are associated with the model 600, and the model 600 of the anatomic structure of the patient P includes a plurality of model paths 606. Each model path 606 of the plurality of model paths 606 is associated with a portion of the plurality of model points 604. As described in the preceding embodiments, the anatomic structure of the patient P may include more than one anatomic structure, the plurality of model points 604 and the plurality of model paths 606 being associated with each of the anatomic structures of the anatomy of the patient P.

At process 704, and with reference to FIGS. 6D-6F, a set of measured points 608 are collected using, for example, an elongate device 310. The set of measured points 608 are associated with a first portion of the anatomic structure of the patient P and are collected from the elongate device 310 while the elongate device, or medical instrument 310 is disposed within the anatomic structure of the patient P. In this example, each of the measured points 608 in the collected set of measured points 608 is associated with one of a plurality of motion cycles of the elongate device 310. As described in the preceding embodiments, each of the motion cycles of the elongate device 310 includes an insertion and a retraction cycle of the elongate device 310, which may be a medical instrument including an elongated flexible body. Additionally, the elongate device 310 may include a sensor. In at least some embodiments, the sensor may include at least one of electromagnetic sensor coupled to the elongate device 310 and a shape sensor.

As further described herein, the collected set of measured points 608 may be collected from observations at a distal end 318 of the elongate device 310 or from the shape sensor of the elongate device 310. That is, the shape sensor may record observed shapes of the elongate device 310 at various times, and measured points 608 may be derived by analyzing the observed shapes of the elongate device 310 in conjunction with a known location of a point along the length of the elongate device 310 or in fixed relation thereto. For example, proximal point 316 of FIGS. 3A-3B may be used to determine a location of any point along the length of the elongate device 310 based on an observed shape. Additionally, the control system (e.g., control system 112) may further be configured to filter the measured points 608 to generate a filtered set of the measured points 608 that includes only measured points 608 that were measured at a selected phase of anatomical movement of the anatomy of the patient P. In some embodiments, the selected phase of anatomical movement used to generate the filtered set of the measured points 608 includes an expiration phase of a breathing cycle of a lung of the patient P (e.g., the lung 400).

At process 706, and with reference to FIG. 6G, the set of measured points 608 associated with a first motion cycle of the plurality of motion cycles are mapped to a first model path 606*a* of the plurality of model paths 606 generated for the model 600. As described in the preceding embodiments, the first model path 606*a* may include a plurality of adjoining model links 605 connected in series including a plurality of model points 604, for example, the model links 605*a*, 605*b*, 605*c*, and 605*e*. In at least some embodiments, the model path 606 that the measured points 608 are associated with may include one or any other number of adjoining, in-series model links 605, each of the model links 605 including any number of the model points 604.

At process 708, and with reference to FIG. 6H, the set of measured points 608 is registered with the portion of the plurality of model points 604 mapped to the first model path 606*a* of the plurality of model paths 606. As described herein, the set of measured points 608 may be registered with the portion of the plurality of model points 604 using a number of processes including the use of rigid and/or non-rigid transforms, a point set registration method (e.g., iterative closes point (ICP) technique), or any other number of registration processes within the scope of this disclosure.

One or more elements in embodiments of this disclosure may be implemented in software to execute on a processor of a computer system such as control processing system. When implemented in software, the elements of the embodiments of the invention are essentially the code segments to perform the necessary tasks. The program or code segments can be stored in a processor readable storage medium or device that may have been downloaded by way of a computer data signal embodied in a carrier wave over a transmission medium or a communication link. The processor readable storage device may include any medium that can store information including an optical medium, semiconductor medium, and magnetic medium. Processor readable storage device examples include an electronic circuit; a semiconductor device, a semiconductor memory device, a read only memory (ROM), a flash memory, an erasable programmable read only memory (EPROM); a floppy diskette, a CD-ROM, an optical disk, a hard disk, or other storage device. The code segments may be downloaded via computer networks such as the Internet, Intranet, etc. Any of a wide variety of centralized or distributed data processing architectures may be employed. Programmed instructions may be implemented as a number of separate programs or subroutines, or they may be integrated into a number of other aspects of the systems described herein. In one embodiment, the control system supports wireless communication protocols such as Bluetooth, IrDA, HomeRF, IEEE 802.11, DECT, and Wireless Telemetry.

Medical tools that may be delivered through the flexible elongate devices or catheters disclosed herein may include, for example, image capture probes, biopsy instruments, laser ablation fibers, and/or other surgical, diagnostic, or therapeutic tools. Medical tools may include end effectors having a single working member such as a scalpel, a blunt blade, an optical fiber, an electrode, and/or the like. Other end effectors may include, for example, forceps, graspers, scissors, clip appliers, and/or the like. Other end effectors may further include electrically activated end effectors such as electrosurgical electrodes, transducers, sensors, and/or the like. Medical tools may include image capture probes that include a stereoscopic or monoscopic camera for capturing images (including video images). Medical tools may additionally house cables, linkages, or other actuation controls (not shown) that extend between its proximal and distal ends to controllably bend the distal end of the instrument. Steerable instruments are described in detail in U.S. Pat. No. 7,316,681 (filed on Oct. 4, 2005) (disclosing "Articulated Surgical Instrument for Performing Minimally Invasive Surgery with Enhanced Dexterity and Sensitivity") and U.S. patent application Ser. No. 12/286,644 (filed Sep. 30, 2008) (disclosing "Passive Preload and Capstan Drive for Surgical Instruments"), which are incorporated by reference herein in their entireties.

The systems described herein may be suited for navigation and treatment of anatomic tissues, via natural or surgically created connected passageways, in any of a variety of anatomic systems, including the lung, colon, the intestines, the kidneys and kidney calices, the brain, the heart, the circulatory system including vasculature, and/or the like.

Note that the processes and displays presented may not inherently be related to any particular computer or other apparatus. Various general-purpose systems may be used with programs in accordance with the teachings herein, or it may prove convenient to construct a more specialized apparatus to perform the operations described. The required structure for a variety of these systems will appear as elements in the claims. In addition, the embodiments of the invention are not described with reference to any particular programming language. It will be appreciated that a variety of programming languages may be used to implement the teachings of the invention as described herein.

In some instances, well known methods, procedures, components, and circuits have not been described in detail so as not to unnecessarily obscure aspects of the embodiments.

This disclosure describes various instruments and portions of instruments in terms of their state in three-dimensional space. As used herein, the term "position" refers to the location of an object or a portion of an object in a three-dimensional space (e.g., three degrees of translational freedom along Cartesian x-, y-, and z-coordinates). As used herein, the term "orientation" refers to the rotational placement of an object or a portion of an object (three degrees of rotational freedom—e.g., roll, pitch, and yaw). As used herein, the term "pose" refers to the position of an object or a portion of an object in at least one degree of translational freedom and to the orientation of that object or portion of the object in at least one degree of rotational freedom (up to six total degrees of freedom). As used herein, the term "shape" refers to a set of poses, positions, or orientations measured along an object.

While certain exemplary embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art.

What is claimed is:

1. A system comprising:

a medical instrument;

a manipulator assembly including one or more actuators configured to move the medical instrument in response to receiving instruction signals;

a tracking system configured to monitor a position of the medical instrument; and a control system including one or more processors communicatively coupled to the manipulator assembly, the medical instrument, and the tracking system, the control system configured to:

generate a plurality of model points from a model of an anatomic structure of a patient, the plurality of model points being associated with coordinates of a model space, wherein the model of the anatomic structure of the patient includes a plurality of model paths, each model path of the plurality of model paths associated with a portion of the plurality of model points;

receive a set of measured points of a first portion of the anatomic structure of the patient from the tracking system while the medical instrument is disposed within the anatomic structure of the patient, wherein at least a portion of the measured points are collected along a length of one or more passageways of the anatomic structure between branch points of adjacent passageways, wherein each measured point of the set of measured points is associated with a first motion cycle of the medical instrument, wherein the first motion cycle includes a single insertion of the medical instrument and a single retraction of the medical instrument;

map each measured point of the set of measured points to a first model path of the plurality of model paths;

register the set of measured points with a first portion of the plurality of model points, the first portion of the plurality of model points associated with the first model path of the plurality of model paths;

based on the registration, generate the instruction signals to operate the manipulator assembly to navigate the medical instrument to a target tissue location during a medical procedure performed using the medical instrument; and transmit the instruction signals to the one or more actuators of the manipulator assembly.

2. The system of claim 1, wherein the first model path includes a plurality of adjoining model links connected in series and including a plurality of model points.

3. The system of claim 1, wherein the tracking system includes a sensor configured to collect the set of measured points.

4. The system of claim 3, wherein the sensor comprises a shape sensor.

5. The system of claim 3, wherein the sensor comprises an electromagnetic sensor coupled to the medical instrument.

6. The system of claim 4, wherein the set of measured points are collected from shape observations for a portion of the medical instrument.

7. The system of claim 1, wherein the set of measured points is collected from observations of a tip of the medical instrument, and wherein the observations are generated by the tracking system.

8. The system of claim 1, wherein the control system is further configured to filter the set of measured points, wherein the filtered set of measured points includes a subset of the set of measured points that includes only measured points measured at a selected phase of anatomical movement.

9. The system of claim 8, wherein the selected phase of anatomical movement is an expiration phase of a breathing cycle of a lung.

10. The system of claim 1, wherein the control system is further configured to:

map each measured point of the set of measured points to a second model path of the plurality of model paths;

determine a first cumulative offset value based on a distance between each measured point of the set of measured points and a respective model point of the plurality of model points associated with the first model path;

determine a second cumulative offset value based on a distance between each measured point of the set of measured points and a respective model point of the plurality of model points associated with the second model path; and based on the first cumulative offset value being less than the second cumulative offset value, select the first model path for the registration.

11. A method comprising:

generating, by a control system of a manipulator assembly, a plurality of model points from a model of an anatomic structure of a patient, the plurality of model points being associated with coordinates of a model space, wherein the model of the anatomic structure of the patient includes a plurality of model paths, each model path of the plurality of model paths associated with a portion of the plurality of model points;

collecting, by the control system, a set of measured points of a first portion of the anatomic structure of the patient from a medical instrument while the medical instrument is disposed within the anatomic structure of the patient, at least a portion of the measured points being collected along a length of one or more passageways of the anatomic structure between branch points of adjacent passageways, wherein each measured point of the set of measured points is associated with a first motion cycle of the medical instrument, wherein the first motion cycle includes a single insertion of the medical instrument and a single retraction of the medical instrument;

mapping, by the control system, each measured point of the set of measured points to a first model path of the plurality of model paths;

registering, by the control system, the set of measured points with a first portion of the plurality of model points, the first portion of the plurality of model points associated with the first model path of the plurality of model paths;

based on the registration, generating, by the control system, instruction signals to operate the manipulator assembly to navigate the medical instrument to a target tissue location during a medical procedure performed using the medical instrument; and moving, by the manipulator assembly, the medical instrument to the target tissue location based on the instruction signals.

12. The method of claim 11, wherein mapping the set of measured points to the first model path includes mapping the set of measured points to a plurality of adjoining model links connected in series.

13. The method of claim 11, wherein the set of measured points are collected from a sensor of the medical instrument.

14. The method of claim 13, wherein the sensor of the medical instrument comprises a shape sensor.

15. The method of claim 13, wherein the sensor comprises an electromagnetic sensor.

16. The method of claim 11, further comprising filtering the set of measured points, wherein filtering the set of measured points includes creating a subset of the set of measured points that includes only measured points measured at a selected phase of anatomical movement.

17. A non-transitory machine-readable medium comprising a plurality of machine-readable instructions which, when executed by one or more processors of a control system of a manipulator assembly, are adapted to cause the one or more processors to perform a method comprising:

generating a plurality of model points from a model of an anatomic structure of a patient, the plurality of model points being associated with coordinates of a model space, wherein the model of the anatomic structure of the patient includes a plurality of model paths, each model path of the plurality of model paths associated with a portion of the plurality of the plurality of model points;

collecting a set of measured points of a first portion of the anatomic structure of the patient from a medical instrument while the medical instrument is disposed within the anatomic structure of the patient, wherein each measured point of the set of measured points is collected along a length of the medical instrument and is associated with a first motion cycle of the medical instrument, wherein the first motion cycle includes a single insertion of the medical instrument a single retraction of the medical instrument;

mapping each measured point of the set of measured points to a first model path of the plurality of model paths;

registering the set of measured points with a first portion of the plurality of model points, the first portion of the plurality of model points associated with the first model path of the plurality of model paths;

based on the registration, generating instruction signals to operate the manipulator assembly to navigate the medical instrument to a target tissue location during a medical procedure; and transmitting the instruction signals to one or more actuators of the manipulator assembly, wherein the manipulator assembly is configured to move the medical instrument based on the instruction signals.

* * * * *